United States Patent
Krastev

(10) Patent No.: US 11,497,575 B1
(45) Date of Patent: Nov. 15, 2022

(54) MULTI-PURPOSE RACK FOR ORGANIZING CONTAINERS/PACKAGES OF DENTAL IMPLANT PLATFORMS FOR EACH TOOTH

(71) Applicant: Pavel Krastev, New Hyde Park, NY (US)

(72) Inventor: Pavel Krastev, New Hyde Park, NY (US)

(*) Notice: Subject to any disclaimer, the term of this patent is extended or adjusted under 35 U.S.C. 154(b) by 541 days.

(21) Appl. No.: 16/591,748

(22) Filed: Oct. 3, 2019

Related U.S. Application Data

(63) Continuation-in-part of application No. 15/263,705, filed on Sep. 13, 2016, now abandoned, which is a
(Continued)

(51) Int. Cl.
*A61B 50/22* (2016.01)
*A61B 50/33* (2016.01)
(Continued)

(52) U.S. Cl.
CPC .......... *A61B 50/33* (2016.02); *A47F 7/0028* (2013.01); *A61B 50/20* (2016.02); *A61B 50/22* (2016.02);
(Continued)

(58) Field of Classification Search
CPC .... A47F 7/0021; A47F 7/0028; A47B 81/007; A61B 50/22; A47J 47/16
(Continued)

(56) References Cited

U.S. PATENT DOCUMENTS

| 364,623 | A | | 6/1887 | Beidler | |
|---|---|---|---|---|---|
| 1,188,146 | A | * | 6/1916 | Ley | ........................ A47B 73/00 211/74 |

(Continued)

FOREIGN PATENT DOCUMENTS

| EP | 2 564 798 | 6/2013 |
|---|---|---|
| GB | 2418 421 | 3/2006 |

OTHER PUBLICATIONS

Press Fit Forces Stress Design Calculator, Jun. 18, 2018, available at: www.engineersedge.com/calculators/machine-design/press-fit/press-fit.htm.
(Continued)

*Primary Examiner* — Jennifer E. Novosad
(74) *Attorney, Agent, or Firm* — Thomas A. O'Rourke; Bodner & O'Rourke, LLP

(57) ABSTRACT

A rack organizes dental implant containers both when housed within intermediate packaging and when removed therefrom, being arranged according to a tooth intended to receive the dental implant within the container. The rack includes: upper and lower flanges, and a connecting flange that separates the upper and lower flanges. The upper flange and connecting flange are each formed with a plurality of openings shaped to receive the dental implant container therethrough when the container is removed from the intermediate packaging. The openings may each have first and second slots to accommodate receiving a container therethrough when housed within intermediate packaging. The lower flange may removably couple to a base with a plurality of recesses, being usable to assist with restorative procedures relating to fixing dental implants, and may be removably coupled to the lower flange with the plurality recesses aligned with a plurality of openings in the lower flange.

15 Claims, 22 Drawing Sheets

Related U.S. Application Data continuation of application No. 13/959,963, filed on Aug. 6, 2013, now Pat. No. 9,545,297.

(60) Provisional application No. 62/740,448, filed on Oct. 3, 2018, provisional application No. 61/692,789, filed on Aug. 24, 2012.

(51) Int. Cl.

| | | |
|---|---|---|
| *B65D 21/02* | (2006.01) | |
| *A61B 90/94* | (2016.01) | |
| *A61C 8/00* | (2006.01) | |
| *A61C 19/02* | (2006.01) | |
| *A61B 50/20* | (2016.01) | |
| *A61B 50/31* | (2016.01) | |
| *A61J 1/03* | (2006.01) | |
| *A61J 1/00* | (2006.01) | |
| *A47F 7/00* | (2006.01) | |
| *A61B 50/00* | (2016.01) | |
| *A61B 50/30* | (2016.01) | |
| *A61B 50/18* | (2016.01) | |
| *A47B 81/00* | (2006.01) | |

(52) U.S. Cl.
CPC ............ *A61B 50/31* (2016.02); *A61B 90/94* (2016.02); *A61C 8/0081* (2013.01); *A61C 8/0087* (2013.01); *A61C 19/02* (2013.01); *A61J 1/00* (2013.01); *A61J 1/03* (2013.01); *B65D 21/0201* (2013.01); *A47B 81/007* (2013.01); *A61B 2050/0056* (2016.02); *A61B 2050/185* (2016.02); *A61B 2050/3011* (2016.02); *A61B 2050/3015* (2016.02); *A61B 2050/311* (2016.02)

(58) Field of Classification Search
USPC .............. 211/85.18, 85.13, 60.1, 70.6, 85.4; 206/564, 562, 563, 369
See application file for complete search history.

(56) References Cited

U.S. PATENT DOCUMENTS

| | | | | |
|---|---|---|---|---|
| 1,226,231 A * | 5/1917 | Mack | .................... | A47K 1/09 206/229 |
| 1,437,596 A * | 12/1922 | Korb | .................... | A61C 3/04 D19/85 |
| 1,446,921 A * | 2/1923 | Montag | .................... | A61C 3/04 206/369 |
| 1,634,953 A * | 7/1927 | Mccune | .................... | B64D 1/02 211/74 |
| 2,298,577 A * | 10/1942 | Mcphail | .................... | A23G 9/227 248/500 |
| 2,383,367 A | 8/1945 | Brown | | |
| 2,587,226 A * | 2/1952 | Rodman | .................... | B25H 3/04 211/65 |
| 2,616,558 A * | 11/1952 | Kay, Jr. | .................... | A24F 9/14 211/70.1 |
| 2,754,008 A * | 7/1956 | Culver | .................... | A47G 21/14 211/70.1 |
| 2,855,107 A * | 10/1958 | Roth | .................... | B25H 3/00 40/658 |
| 3,033,355 A | 5/1962 | Van Sickle | | |
| 3,062,380 A * | 11/1962 | Grela | .................... | B01L 9/06 211/73 |
| 3,163,287 A * | 12/1964 | Barnett | .................... | A47G 23/0641 224/540 |
| 3,269,788 A | 8/1966 | Williams | | |
| 3,289,829 A * | 12/1966 | Donahue | .................... | B65D 85/44 206/592 |
| 3,298,531 A * | 1/1967 | Wilcke | .................... | A47L 13/512 211/70.6 |
| 3,324,996 A | 6/1967 | Jordi | | |
| 3,397,671 A | 8/1968 | Hartman, Jr. | | |
| 3,402,850 A | 9/1968 | Barton | | |
| 3,407,454 A | 10/1968 | Myatt | | |
| 3,565,323 A * | 2/1971 | Katzenmeyer | ........ | B65D 71/004 229/117.14 |
| 3,630,171 A | 12/1971 | Huck | | |
| 3,643,812 A * | 2/1972 | Mander | .................... | B01L 9/06 220/519 |
| 3,751,172 A * | 8/1973 | Seitz | .................... | B01L 9/06 356/244 |
| 3,807,954 A * | 4/1974 | McDonald | .................... | A61L 2/26 206/563 |
| 3,847,277 A * | 11/1974 | Doner | .................... | A45C 1/12 D11/147 |
| 3,861,867 A * | 1/1975 | Ouhl | .................... | A61C 13/14 269/53 |
| 3,975,803 A | 8/1976 | Katayama | | |
| D243,559 S * | 3/1977 | Hoyle | ............. | D28/38 |
| 4,026,588 A | 5/1977 | Bisbing | | |
| 4,038,937 A | 8/1977 | Moe | | |
| 4,057,309 A | 11/1977 | Fragale | | |
| 4,084,695 A | 4/1978 | Halbich | | |
| 4,151,912 A * | 5/1979 | Harrold | .................. | B25H 3/003 206/443 |
| 4,294,348 A | 10/1981 | Hastings | | |
| 4,294,931 A * | 10/1981 | Levin | .................... | C12Q 1/16 206/362 |
| 4,310,094 A * | 1/1982 | Hotchkiss, Jr. | ........ | A47F 5/0884 D8/367 |
| 4,318,477 A * | 3/1982 | Kerpe | .................... | A61J 7/0084 206/534 |
| 4,372,445 A | 2/1983 | Keffeler | | |
| 4,446,972 A * | 5/1984 | Sussman | ............... | A47G 29/08 211/60.1 |
| 4,453,639 A * | 6/1984 | Sharma | .................... | B01L 9/06 422/561 |
| 4,535,897 A * | 8/1985 | Remington | ............. | B25H 3/00 211/74 |
| 4,593,819 A | 6/1986 | Will | | |
| 4,653,637 A * | 3/1987 | Wallace | .................... | B25H 3/04 211/70.1 |
| 4,667,822 A * | 5/1987 | Coopmans | ............... | B25H 3/02 312/334.44 |
| 4,681,219 A * | 7/1987 | Kitchens | ................ | A01K 97/06 224/406 |
| 4,722,440 A * | 2/1988 | Johnston | ................ | B65D 71/70 206/319 |
| 4,735,318 A | 4/1988 | Keffeler | | |
| 4,793,492 A | 12/1988 | Halbich | | |
| 4,817,819 A | 4/1989 | Kelly | | |
| 4,872,559 A | 10/1989 | Schoon | | |
| 4,893,722 A | 1/1990 | Jones | | |
| 4,907,705 A * | 3/1990 | Waldeck | ............... | A47F 7/0028 211/195 |
| 4,947,984 A * | 8/1990 | Kaufman | ............ | G11B 33/0494 206/214 |
| 4,951,832 A | 8/1990 | Tenney | | |
| 4,966,288 A * | 10/1990 | Kirkham | .................. | B25H 3/04 211/13.1 |
| 4,966,599 A | 10/1990 | Pollock | | |
| 4,997,090 A | 3/1991 | Lenmark et al. | | |
| 4,998,623 A | 3/1991 | Doull | | |
| 5,011,018 A | 4/1991 | Keffeler | | |
| 5,025,935 A * | 6/1991 | Hadachek | ............... | B63C 11/02 224/543 |
| 5,109,984 A * | 5/1992 | Romick | ............. | B65D 83/0463 206/532 |
| 5,129,528 A * | 7/1992 | Eidsmoe | ................ | B25H 3/003 211/70.6 |
| 5,133,939 A * | 7/1992 | Mahe | .................... | B01L 9/06 211/74 |
| 5,141,117 A * | 8/1992 | Olsen | .................... | A47F 7/0028 211/74 |
| 5,152,406 A * | 10/1992 | Kling | .................... | B25H 3/04 222/173 |
| 5,174,451 A | 12/1992 | Niven | | |

(56) References Cited

U.S. PATENT DOCUMENTS

| | | | |
|---|---|---|---|
| 5,267,650 A | 12/1993 | Gilbilisco | |
| 5,348,158 A | 9/1994 | Honan | |
| 5,358,112 A * | 10/1994 | Gardner | A61C 3/04 206/443 |
| 5,394,988 A * | 3/1995 | Edwards | B65D 71/70 206/562 |
| 5,409,667 A * | 4/1995 | Elson | C12M 23/48 211/74 |
| 5,422,273 A * | 6/1995 | Garrison | C12M 33/02 422/547 |
| 5,553,712 A | 9/1996 | Tisbo | |
| 5,558,229 A | 9/1996 | Halbich | |
| 5,575,399 A | 11/1996 | Intini | |
| 5,617,960 A * | 4/1997 | Bishop | A47B 97/02 211/44 |
| 5,641,079 A * | 6/1997 | Schmidt | A47F 5/0823 211/104 |
| 5,735,406 A | 4/1998 | Romick | |
| 5,765,690 A * | 6/1998 | Baxter | B65D 71/72 229/198.2 |
| 5,829,590 A * | 11/1998 | Klein | A61C 3/04 206/443 |
| 5,833,072 A | 11/1998 | Lambelet, Jr. | |
| 5,843,388 A * | 12/1998 | Arroyo | A61L 2/26 206/370 |
| 5,878,757 A | 3/1999 | Hernandez | |
| 5,890,613 A | 4/1999 | Roberts | |
| 5,967,323 A * | 10/1999 | Siragusa | B65D 25/108 220/780 |
| 5,992,912 A * | 11/1999 | Zimm | A45D 44/04 220/756 |
| 6,021,901 A | 2/2000 | Wolfe | |
| 6,056,120 A * | 5/2000 | Hollingsworth | A47F 7/0028 211/70.1 |
| 6,250,480 B1 * | 6/2001 | McGuinness | A47F 7/0028 D6/552 |
| 6,328,746 B1 | 12/2001 | Gambale | |
| 6,354,447 B1 * | 3/2002 | Brown | A45D 44/005 132/73 |
| 6,471,060 B1 | 10/2002 | Leyshon | |
| 6,484,892 B1 * | 11/2002 | Gooner | B25H 3/04 248/176.2 |
| 6,564,945 B1 | 5/2003 | Weinstein et al. | |
| 6,758,338 B2 | 7/2004 | Lien | |
| 6,779,663 B1 | 8/2004 | Pocsi | |
| 6,959,806 B2 | 11/2005 | Barker | |
| 7,004,324 B1 | 2/2006 | Delorio | |
| 7,036,668 B2 * | 5/2006 | Udy | B25H 3/04 211/60.1 |
| 7,097,037 B1 | 8/2006 | Keffeler | |
| 7,158,011 B2 | 1/2007 | Brue | |
| 7,188,629 B2 * | 3/2007 | Mehes | A47K 1/09 206/209.1 |
| 7,228,966 B1 | 6/2007 | Turner | |
| 7,240,798 B1 * | 7/2007 | Chiang | B65D 25/101 206/562 |
| 7,258,240 B2 * | 8/2007 | Wescott, III | B01L 9/06 211/74 |
| 7,367,451 B2 | 5/2008 | Pendergraph | |
| 7,497,351 B2 | 3/2009 | Amundson | |
| 7,624,890 B2 | 12/2009 | Noble | |
| 7,793,785 B2 | 9/2010 | Keffeler | |
| 7,877,268 B2 | 1/2011 | Kulkarni | |
| 8,215,480 B2 * | 7/2012 | Qian | B01L 9/06 211/85.13 |
| 8,997,995 B2 * | 4/2015 | Chitsazan | A47G 23/0208 206/541 |
| D743,837 S * | 11/2015 | Zand | D11/146 |
| 9,282,817 B2 * | 3/2016 | Yates | A47B 81/005 |
| 9,545,297 B1 * | 1/2017 | Krastev | A61J 1/00 |
| 10,172,484 B2 * | 1/2019 | Maldonado | A47F 7/06 |
| 10,342,391 B2 * | 7/2019 | Beckerman | A47F 1/085 |
| D887,489 S * | 6/2020 | Nucci | D19/84 |
| 10,669,195 B2 * | 6/2020 | Abbott, Jr | B08B 9/42 |
| 2003/0116516 A1 * | 6/2003 | Belokin | A47F 7/0028 211/70.1 |
| 2003/0159319 A1 | 8/2003 | Ransom et al. | |
| 2003/0222036 A1 * | 12/2003 | Lacombe | B25H 3/003 211/70.6 |
| 2004/0089581 A1 | 5/2004 | Dienst | |
| 2004/0144739 A1 * | 7/2004 | Marek | B25H 3/04 211/89.01 |
| 2007/0062964 A1 | 3/2007 | Kampf et al. | |
| 2008/0251476 A1 * | 10/2008 | Shiao | B25H 3/04 211/70.6 |
| 2009/0272703 A1 * | 11/2009 | Conway, Jr. | A47F 7/0028 211/85.4 |
| 2009/0281657 A1 | 11/2009 | Gak | |
| 2009/0314728 A1 * | 12/2009 | Oshry | A45D 44/04 211/85.18 |
| 2010/0200527 A1 * | 8/2010 | Hernandez | A47F 7/0028 211/70.6 |
| 2010/0200583 A1 * | 8/2010 | Curtin | B65D 45/20 220/666 |
| 2010/0288659 A1 * | 11/2010 | Dang | A47K 1/09 206/362.1 |
| 2013/0001180 A1 * | 1/2013 | Stout | A61B 50/20 211/85.13 |
| 2013/0015097 A1 * | 1/2013 | Thornton | A47G 23/0641 206/563 |
| 2013/0026056 A1 | 1/2013 | Key | |
| 2013/0112635 A1 * | 5/2013 | Tsukaguchi | B25H 3/04 211/70.6 |
| 2013/0213912 A1 * | 8/2013 | Naha | A01G 31/02 211/85.4 |
| 2014/0021086 A1 | 1/2014 | Roesler | |
| 2014/0251862 A1 * | 9/2014 | Priebe | A61J 1/03 206/534 |
| 2014/0363555 A1 * | 12/2014 | Simpson | B65D 5/5038 426/420 |
| 2015/0041417 A1 * | 2/2015 | Christenson | A47F 5/08 211/85.18 |

OTHER PUBLICATIONS

"Three General Types of Fit," available at www.mmto.org/dclark/Reports/Encoder%20Upgrade/fittolerences%20%5BRead-Only%5D.pdf., Jul. 8, 2019.

"Engineering Fit," available at: https://en.wikipedia.org/wiki/Engineering_fit, Jul. 8, 2019.

* cited by examiner

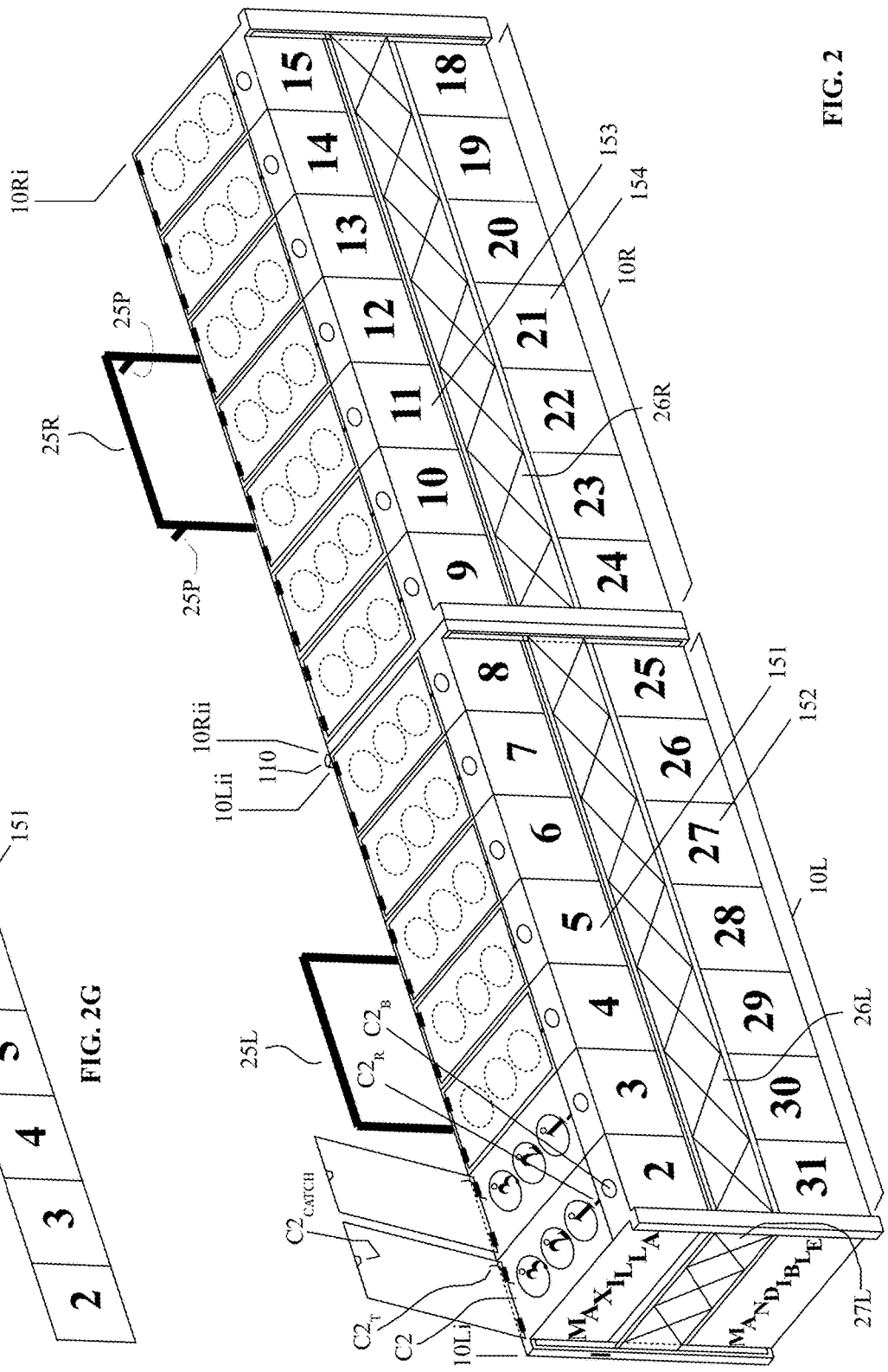
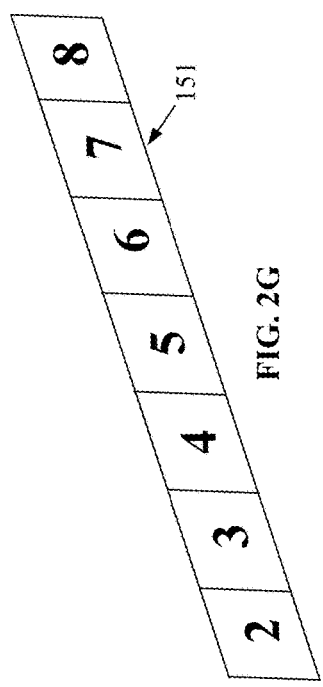
FIG. 2G
FIG. 2

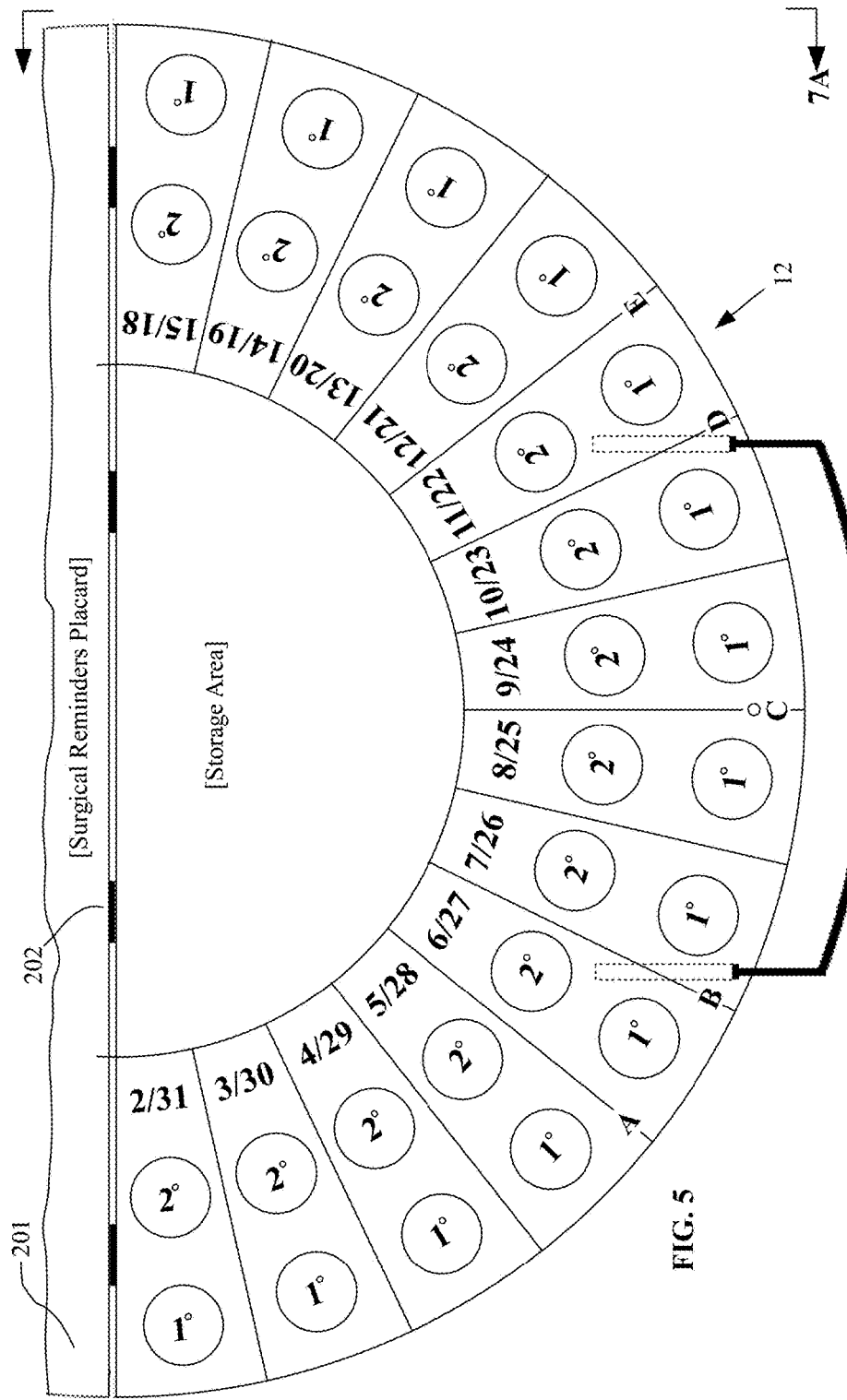

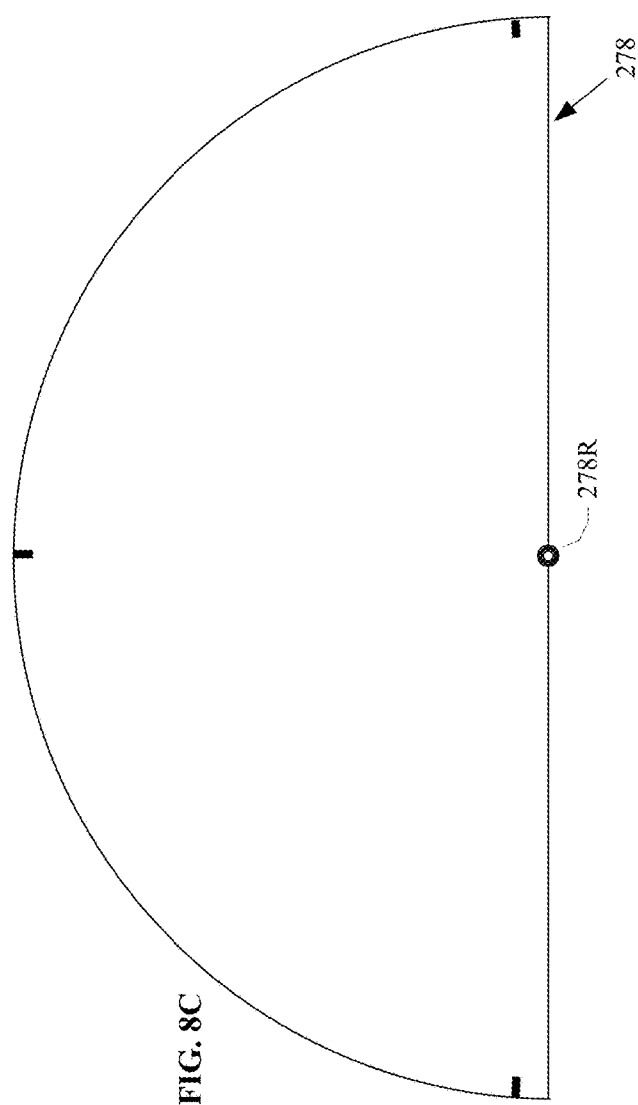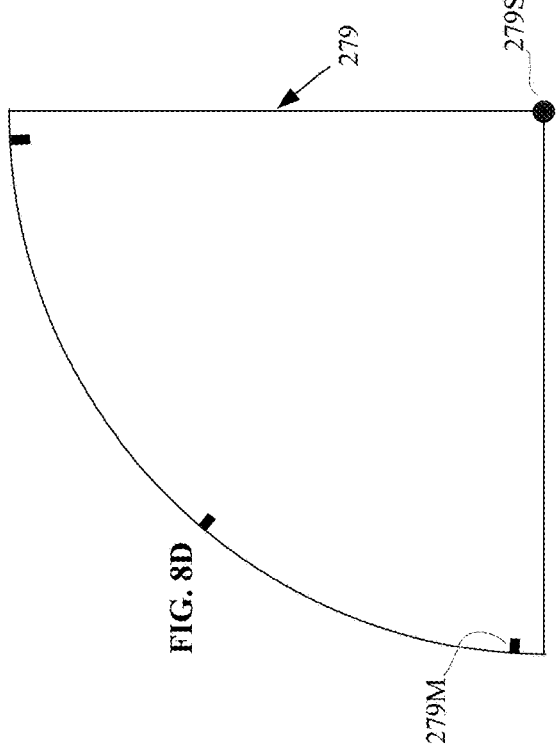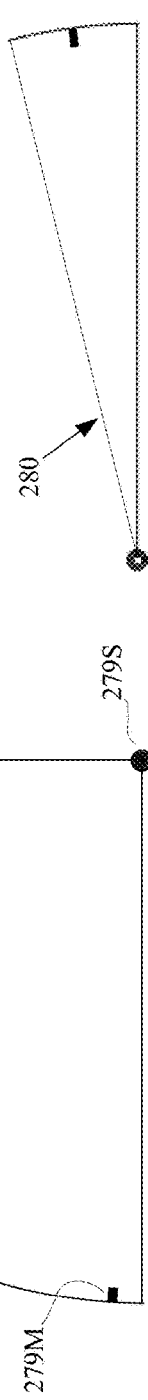

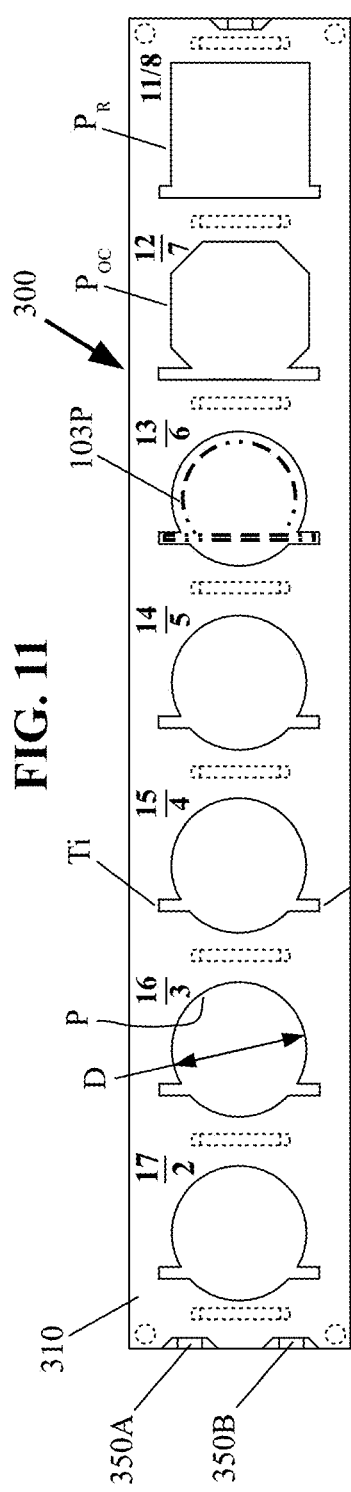
FIG. 11
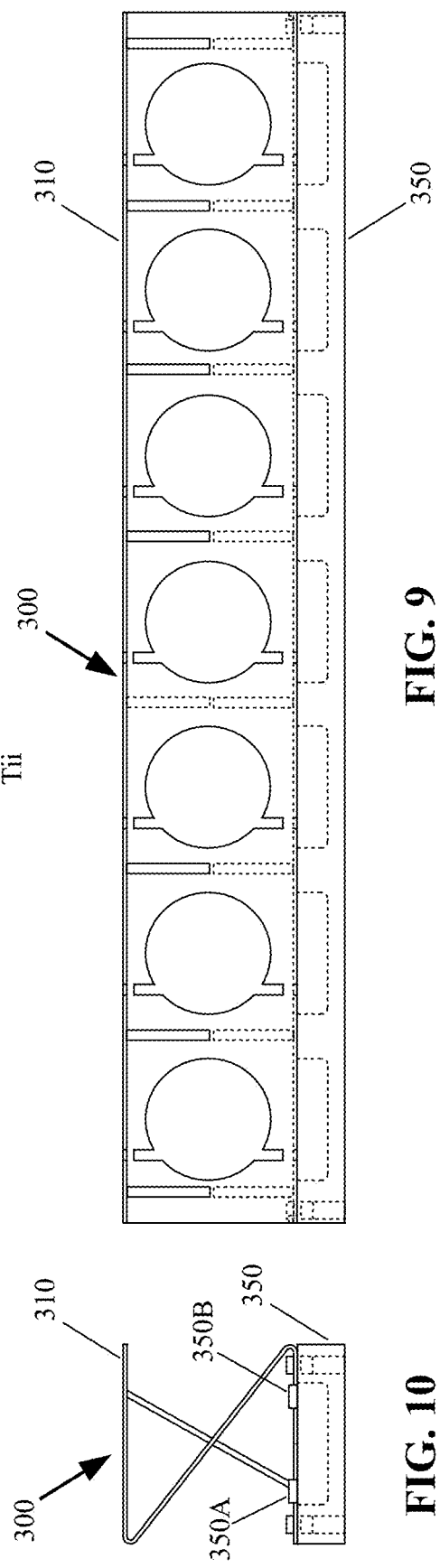
FIG. 9
FIG. 10

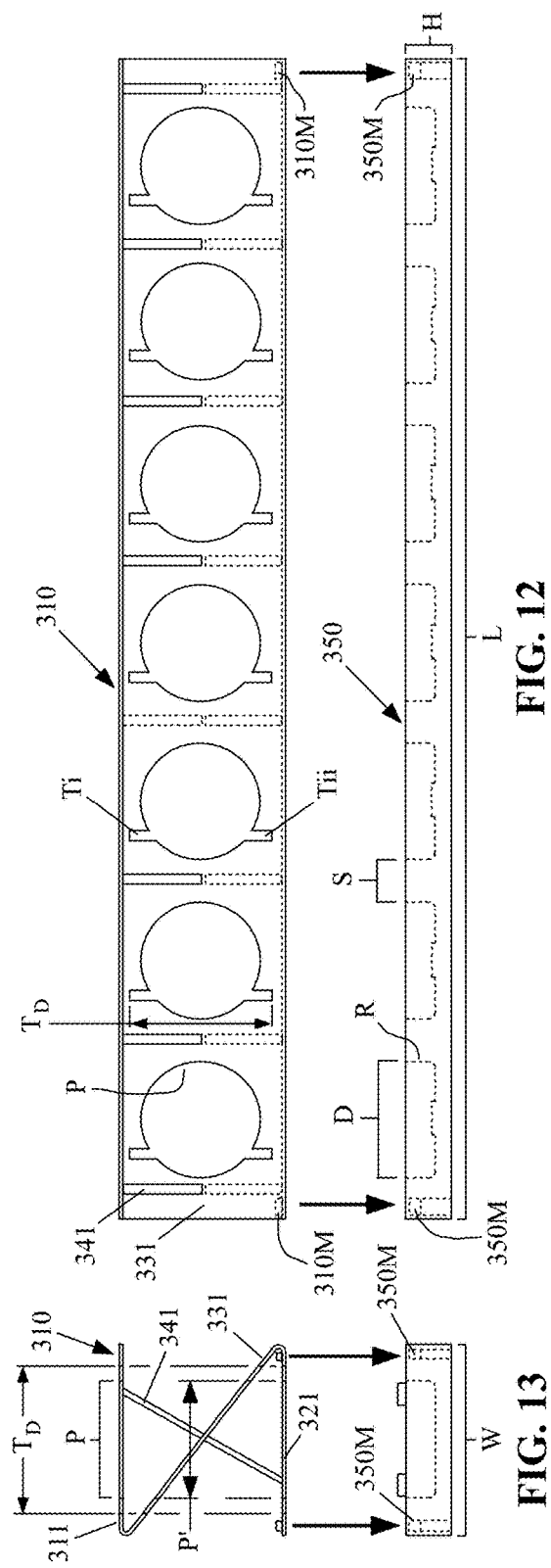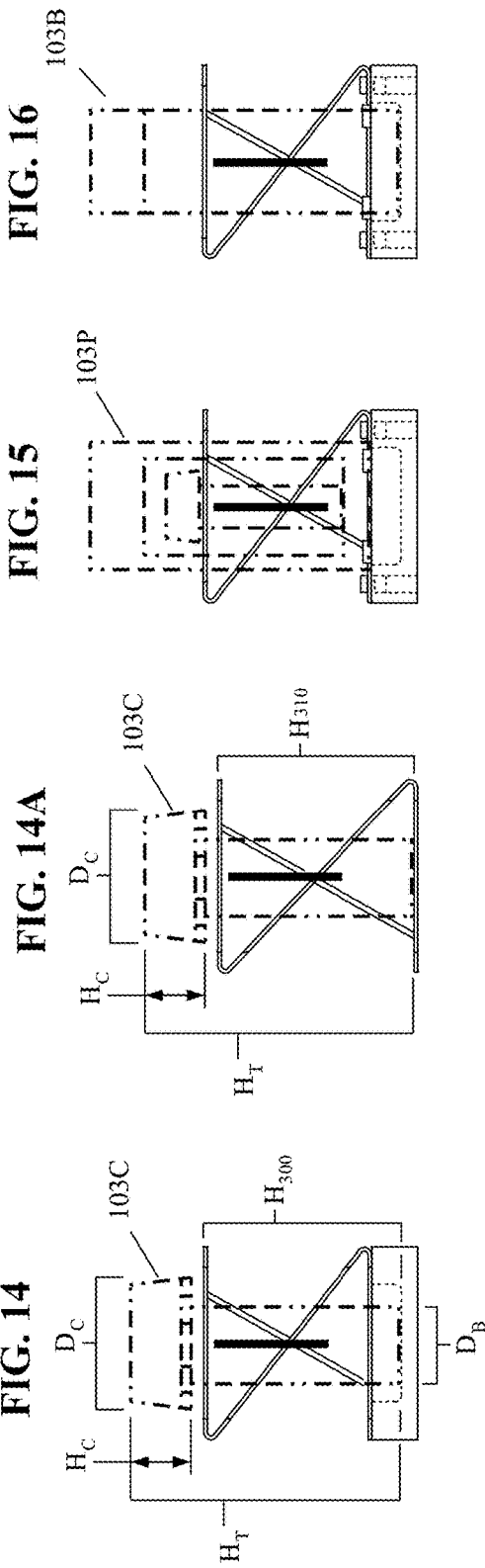

MULTI-PURPOSE RACK FOR ORGANIZING CONTAINERS/PACKAGES OF DENTAL IMPLANT PLATFORMS FOR EACH TOOTH

CROSS REFERENCES TO RELATED APPLICATIONS

This application claims priority on U.S. Provisional Application Ser. No. 62/740,448, filed on Oct. 3, 2018, and this application is also a continuation in part of U.S. application Ser. No. 15/263,705, filed on Sep. 13, 2016, which is a continuation of U.S. application Ser. No. 13/959,963, filed on Aug. 6, 2013, now issued as U.S. Pat. No. 9,545,297, which claims priority on U.S. Provisional Application Ser. No. 61/692,789, filed on Aug. 24, 2012, all disclosures of which are incorporated herein by reference.

FIELD OF THE INVENTION

The present invention relates to improvements in dental implant surgery, and more particularly to apparatus which is adapted to aid an oral surgeon in organizing implants for a patient's procedure, and to help prevent dropping of implants, to help increase the speed of the procedure, and to reduce the likelihood of the surgeon inadvertently deviating from the intended procedure by eliminating confusion as to which implant belongs in a given site.

BACKGROUND OF THE INVENTION

There are many conditions which may result in a person becoming partially or completely edentulous (periodontal disease, an injury, etc.), which in the past had been remedied by the wearing of a prosthetic device, known as dentures. Dentures were constructed to replace the missing teeth and were supported by surrounding teeth and/or by the underlying tissue. The significant drawbacks to the wearing of such partial or complete dentures, principally its means of support, which often required the use of adhesives, as well as its cleaning requirements, served to bolster the development of dental implants.

Today's dental implants are typically root form endosseous (in the bone), being a "root" device (a screw) that is usually made of titanium, and which is inserted into the jaw through the bone at the alveolar ridges. After a healing period, an abutment is attached thereto and may protrude through the periostium and receive a prosthodontic appliance—a new tooth.

It is not uncommon for an implant procedure to be performed on both the maxilla (upper jaw) and the mandible (lower jaw), and in some cases, enough titanium screws may be implanted to replace all of the missing teeth of a completely edentulous person. Although there need not be a corresponding implant screw for each prosthodontic tooth installed, and for the maxilla, where bone density is poorer than the lower jaw, the number of implants will depend on the quality and volume of bone at each prospective implant site. An oral surgeon will generally place 8-10 implants to support a complete set of 14 replacement teeth for the upper jaw. This is done when the final prosthetic device is fixed and only retrievable by the restorative dentist. The same applies to the lower jaw, but a full fixed case can be done with fewer implants, as the lower jaw is generally more favorable for implants in terms of its bone density. Generally, when fabricating a removable prosthesis that is implant supported, 6 implants are used in the upper jaw, and 2 or 4 implants are used in the lower anterior jaw. Each site will require individual preparation and an implant screw, referred to as a "platform." where the platform's diameter and length is optimum for the geometry of that particular site.

As a general rule, greater strength and better result are obtained for the subsequently installed prosthodontic teeth, by implanting the longest platform with the largest diameter that the bone is able to support locally. Because the physiology of the jaw bones normally varies at different locations throughout the mouth, a range of different size implants may be used at each location. In the front of the mouth, shorter and narrower implants are generally used, and often have diameters in the range of 3.5 mm to 4.2 mm. If a particular patient has an unusually narrow space between two teeth, a "mini dental implant," being in the range of 2 mm to 3.5 mm, may be used. Towards the back of the mouth, the bone that supports the molars may require implants diameters in the range of 4.5 mm to 6.0 mm, as that is where the strength of the tooth is crucial for mastication. For a full technical discussion of the rationale for particular implant platform sizing, see Contemporary Implant Dentistry, by Carl E. Misch, $3_{rd}$ Ed., p. 160-177, the disclosures of which are incorporated herein by reference.

The surgeon may make a final selection for each implant platform during the procedure, depending upon final measurements taken of the bone after formation of the implant hole (osteotomy). Variations from a "recommended" platform size are frequently necessary, especially if a "spinner" occurs, which is an implant that does not have good primary fixation. In that case, a wider implant fixture must be placed to achieve proper primary stability. Therefore, the number of different sized/shaped platforms that the oral surgeon may need to have readily available during a procedure, to accommodate all of the implant sites, may often become considerable and unwieldy.

The concerns regarding the health and safety of the dental implant patient are as significant as with any other surgery being performed today. The dental implant surgeon is concerned with many things, including infection at the site of the implant, the potential injury/damage to surrounding blood vessels or teeth, the possibility of nerve damage, the potential for sinus problems when the platform protrudes into one of the sinus cavities, as well as the potential for loss of an implant or fracturing of a patients jaw. The diligent oral surgeon performing implant procedures is thus confronted by an array of issues that must be successfully negotiated in order to meet the accepted standard of practice, many of which principally relate to forming an optimally sized implant hole (osteotomy) for installation of the optimally sized platform (optimal length and width of the implant).

Where the patient requires multiple platforms to be implanted, and with the probability of needing to vary the platform selected for implantation from the "recommended" platform size, the potential for an error resulting in malpractice escalates. Furthermore, increased handling of the vials that contain the platform in a sterile environment also introduces the likelihood of its mishandling, which may result in dropping of the vial and ruining of the sterile seal, which would necessitate the use of a new implant, at additional cost.

The current invention seeks to organize the array of implants that may be used during surgery. The current invention allows an oral surgeon to be well prepared prior to surgery and during the surgery for any deviation from a planned implant size.

OBJECTS OF THE INVENTION

It is an object of the invention to provide a means of organizing dental implant platforms for an oral surgeon.

It is another object of the invention to provide a case that sorts dental implant platforms according to their use in the maxilla and/or the mandible.

It is a further object of the invention to provide a case that sorts dental implant platforms according to their use in respective tooth locations for both the maxilla and the mandible.

It is another object of the invention to provide a series of appropriate back-up implants.

It is a further object of the invention to properly orient the surgeon during the surgery, and eliminate confusion, as to the planned implant sites for a set of platforms.

It is another object of the invention to provide a means of visually identifying the intended tooth/jaw location for each of the dental implants stored in a case.

It is also an object of the invention to provide a means of collapsing a dental implant case for its transport or storage, and for expanding the case for more advantageous use during an implant procedure.

Further objects and advantages of the invention will become apparent from the following description and claims, and from the accompanying drawings.

SUMMARY OF THE INVENTION

A dental implant surgery organizer case is disclosed for organizing the multitude of implant platforms that may need to be readily available to an oral surgeon during the performance of implant procedures. The dental implant organizer may comprise an elongated left-side case being pivotally attached to an elongated right-side case, where the left-side case and the right-side case may pivot 180 degrees relative to each other, between a collapsed position, in which they are parallel but side-by-side with each other, and an extended position, in which they are parallel, but in line with each other. When occupying the collapsed position, the left-side case and the right-side case may be secured, on the ends opposite from the hinge, using a twist lock and pivotable flange.

Each case may be segregated by a plurality of walls into a series of compartments, and may preferably have seven compartments that are accessible from the top of the case. Each compartment may be adapted to support one or more implant platform vials. Each of the compartments may preferably support three or more such vials, which may contain the suggested implant platform and two other possible alternatively sized platforms that are likely to be needed by the surgeon as an alternate, depending upon quality and volume of the patient's bone at each prospective implant site. Each compartment may also preferably have a hinged lid that is biased into an open position, permitting easy access to the vials therein. The hinged lid may be retained in the closed position by a simple catch mechanism that may be actuated by the touching of a respective button on the top of the case. Each lid may preferably be translucent, to permit the practitioner or an assistant of the practitioner to recognize that an implant within the case has been utilized for a previous procedure, and that it needs to be replaced before using the case again.

The upper front of the left-side case may receive a placard or have stenciled thereon, tooth numbers for respective compartments, for the teeth of a patient's upper right side, which, in the American system, would principally be teeth numbers: 2, 3, 4, 5, 6, 7, and 8 (wisdom tooth not included). In the European system (Palmer Notation method) they would be teeth numbers: 7, 6, 5, 4, 3, 2, and 1. The upper front of the right-side case may receive a placard or have stenciled thereon, the tooth numbers for respective compartments for the teeth of a patient's upper left side, which, in the American system, would principally be teeth numbers: 9, 10, 11, 12, 13, 14, and 15 (1, 2, 3, 4, 5, 6, and 7 in the European system). The lower front of the left-side case may receive a placard or have stenciled thereon, the tooth numbers for the teeth of a patient's lower right side, being teeth numbers: 31, 30, 29, 28, 27, 26, and 25 (7-1 in the European system). Finally, the lower front of the right-side case may receive a placard or have stenciled thereon, the tooth numbers for the teeth of a patient's lower left side, being teeth numbers: 24, 23, 22, 21, 20, 19, and 18 (1-7 in the European system).

A slidable shield may be received on the front of both the left-side case and the right-side case, each of which may be slid upward to conceal the teeth numbering for the maxilla, when the case is being used for implants on the patient's mandible, or it may be slid downward to conceal the teeth numbering for the mandible, when the case is being used for implants on the patient's maxilla. A placard or stenciling may also appear on the sides of the case identifying the upper numbering as being for the "MAXILLA," while the another placard or stenciling may identify the lower numbering as being for the "MANDIBLE." A slidable shield located on each end may be used to similarly conceal the MAXILLA" stencil when the case is being used for placing implants within the mandible, or vice versa.

In an alternative embodiment, the left-side case and the right-side case may each have a lower tray that is outwardly slidable with respect to the cases. Each lower tray may contain seven in-line compartments that may preferably support three or more vials, like the upper compartments previously described. Therefore, in this alternative embodiment, the upper compartments may be used to only organize vials of implant platforms for the teeth of the maxilla, while die lower compartments may be used to only organize vials of implant platforms for the teeth of the mandible.

Prior to performing an extensive implant procedure, the oral surgeon or assistant may position the case on a cart in proximity to the surgical chair, and pivot the left-side and right-side cases into the extended, in-line position. The trays may then be slid outwardly to expose the lower compartments. To further assist the surgeon during the procedure, the lids of only the tooth locations to receive implants may be unlatched, thereby permitting biasing of those lids into the open position. The surgeon will therefore have the correct assortment of tooth-specific implant platforms readily available to him/her during the procedure, along with a textual indication of which implant locations—tooth numbers and jaw position (maxilla/mandible)—which those platforms are intended for, to serve as a visual cue during the procedure to help prevent accidental mis-placement of an implant.

Also disclosed is an organizer rack configured to house and arrange both a plurality of dental implant containers (e.g., at least 7 containers) when housed within intermediate packaging and when removed from the intermediate packaging, being arranged according to a tooth number intended to receive the dental implant within the respective container. The organizer rack may include: an upper flange, a lower flange, and a connecting flange. The upper flange may be formed with a plurality of openings, each of the openings comprising a substantially circular shape or other shapes (e.g., polygonal) that are configured to receive the dental implant container therethrough when the container is removed from the intermediate packaging. Each of the circular or other shaped openings in the upper flange may have a first slot and a second slot, with the first slot configured to extend away from a first side of the shaped opening, and the second slot configured to extend away from a second side of the shaped opening being directly opposite and substantially aligned with the first slot. The shaped opening and the first and second slots are configured to receive the dental implant container therethrough when housed within intermediate packaging. The lower flange is configured to support the dental implant containers, and the connecting flange is configured to extend from and be joined to a portion of each of the lower flange and the upper flange to support the upper flange at a distance away from the lower flange for a top of the dental implant container to protrude a desired amount beyond a top of the upper flange. The upper flange and the lower flange may be substantially flat and parallel to each other, and each may have a first side and a second side, and the connecting flange may be angled from the first side of the lower flange to the second side of the upper flange to form a z-shaped cross-section. The connecting flange also has a plurality of openings each being aligned to respectively correspond with the plurality of openings in the upper flange, to receive a dental implant container therethrough when housed within intermediate packaging or when removed from the intermediate packaging.

A base portion may be used with the rack to assist with restorative procedures relating to fixing dental implants, and may be removably coupled to and aligned with the lower flange. The lower flange may also be formed to include a plurality of openings each being aligned to respectively correspond with the plurality of openings in the upper flange, and the base portion may be formed with a plurality of recesses configured hold one more materials associated with the restorative procedure for dental implants. The plurality of recesses are also formed to be aligned to respectively correspond with the plurality of openings in the upper flange, with a bottom of each recess in the base portion being configured to receive and provide upward support to a bottom of the dental implant container when removed from the intermediate packaging. The removable coupling may be accommodated in any suitable manner, including, but not limited to, the use of: a plurality of magnets on the lower flange, and a correspondingly positioned plurality of magnets on the base portion to align the lower flange with the base portion; the use of magnetic materials for the lower flange and the base; a plurality of holes on the lower flange and a plurality of correspondingly positioned pins on the base portion; and a protruding flange at a first end of the base and a pair of protruding flanges at a second end of the base, and correspondingly positioned notches at the first and second ends of the lower flange.

BRIEF DESCRIPTION OF THE DRAWINGS

FIG. 2 is the dental implant platform organizer case of FIG. 1, being shown in the extended, in-line position, for use during an implant procedure.

FIG. 2G is a detail view of one of the placards used for the dental implant platform organizer case of FIG. 2.

FIG. 5 is a top view of a second embodiment of the dental implant platform organizer case of the current invention, which may be formed into a semi-circular shape to more closely resemble the positioning of the tooth locations in the patient's mouth.

FIG. 6 is a side view of the dental implant platform organizer case of FIG. 5.

FIG. 8C illustrates a first example of a rotator shield that is usable with the organizer case of FIG. 8A.

FIG. 8D illustrates a second example of a rotator shield that is usable with the organizer case of FIG. 8A.

FIG. 8E illustrates a third example of a rotator shield that is usable with the organizer case of FIG. 8A.

FIG. 9 illustrates a front view of a multi-purpose rack that may be used to organize a plurality of containers and/or packages each of which hold a dental implant platform for a particular tooth, to assist a surgeon during dental implant surgery, and which rack may also be separated for a portion thereof to be used during a restorative procedure for dental implants.

FIG. 10 is an end view of the rack of FIG. 9.

FIG. 11 is a top view of the rack of FIG. 9.

FIG. 12 is the front view of FIG. 9, but is shown prior to the upper and lower portions of the rack being releasably secured together.

FIG. 13 is the end view of FIG. 10, but is shown prior to the upper and lower portions of the rack being releasably secured together.

FIG. 14 is the end view of FIG. 10, but is shown with a dental implant container stored in at least one of the openings.

FIG. 14A is an end view of only the upper portion of the rack being used by itself to support a plurality of dental implant containers therein.

FIG. 15 is the end view of FIG. 10, but is shown with a packaged dental implant container stored in at least one of the openings.

FIG. 16 is the end view of FIG. 10, but is shown with an elongated box-shaped dental implant container stored in at least one of the openings.

DETAILED DESCRIPTION OF THE INVENTION

Figure 1:
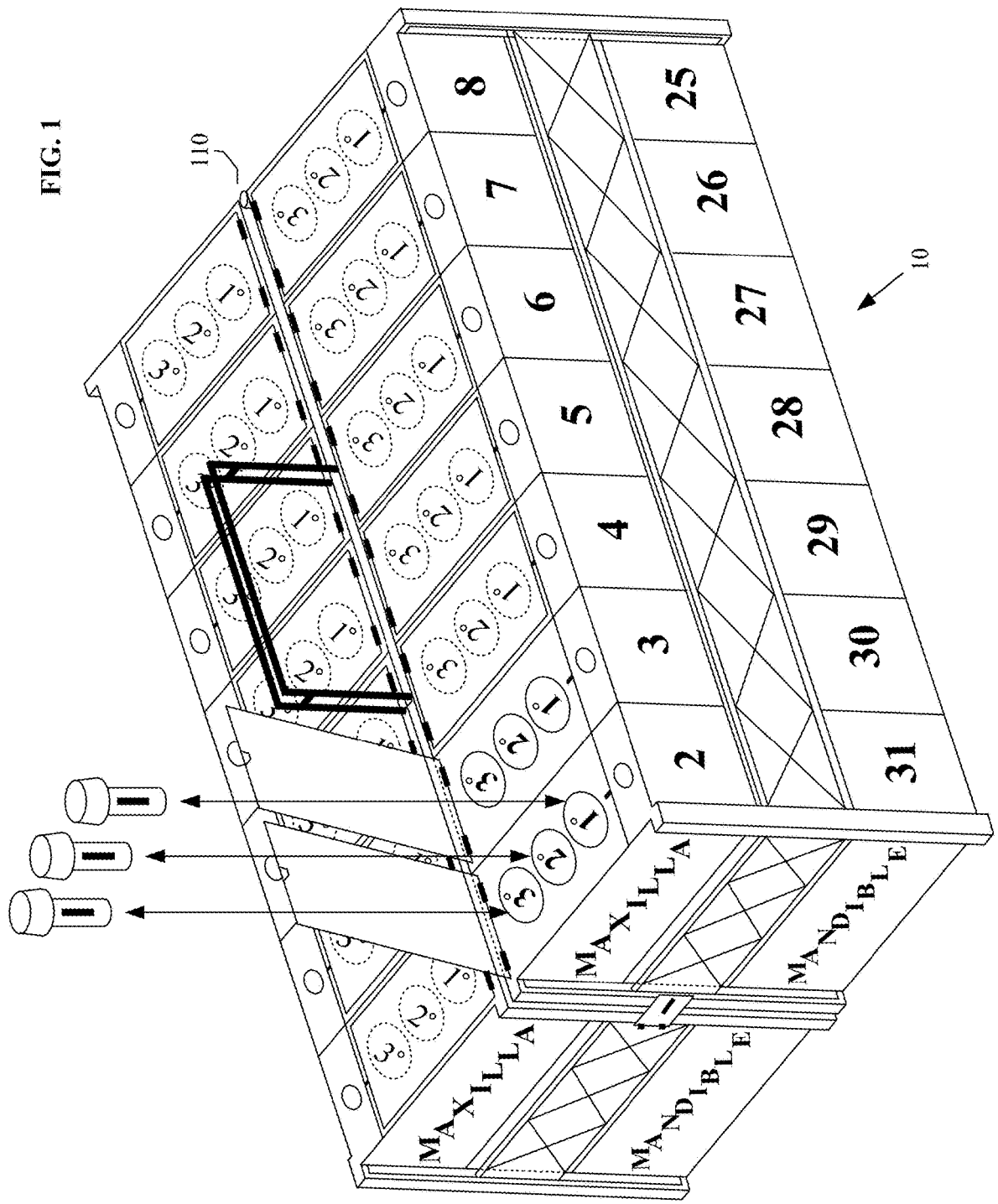
FIG. 1 is a first embodiment of the dental implant platform organizer case of the present invention, being shown in the collapsed position, which is preferable for storage/transport, but is also nonetheless usable during an implant procedure, particularly for a procedure performed on only the left-side or the right-side.

As used throughout this specification, the word "may" is used in a permissive sense (i.e., meaning having the potential to), rather than a mandatory sense (i.e., meaning must), as more than one embodiment of the invention may be disclosed herein. Similarly, the words "include", "including", and "includes" mean including but not limited to.

The phrases "at least one". "one or more", and "and/or" may be open-ended expressions that are both conjunctive and disjunctive in operation. For example, each of the expressions "at least one of A. B and C", "one or more of A, B, and C", and "A, B, and/or C" herein means all of the following possible combinations: A alone; or B alone; or C alone; or A and B together; or A and C together; or B and C together; or A. B and C together.

Also, the disclosures of all patents, published patent applications, and non-patent literature cited within this document are incorporated herein in their entirety by reference. However, it is noted that citing herein of any patents, published patent applications, and non-patent literature is not an admission as to any of those references constituting prior art with respect to the disclosed and/or claimed apparatus/method.

Furthermore, the described features, advantages, and characteristics of any particular embodiment disclosed herein, may be combined in any suitable manner with any of the other embodiments disclosed herein.

Additionally, any approximating language, as used herein throughout the specification and claims, may be applied to modify any quantitative or qualitative representation that could permissibly vary without resulting in a change in the basic function to which it is related. Accordingly, a value modified by a term such as "about" is not to be limited to the precise value specified, and may include values that differ from the specified value in accordance with applicable case law. Also, in at least some instances, a numerical difference provided by the approximating language may correspond to the precision of an instrument that may be used for measuring the value. A numerical difference provided by the approximating language may also correspond to a manufacturing tolerance associated with production of the aspect/feature being quantified. Furthermore, a numerical difference provided by the approximating language may also correspond to an overall tolerance for the aspect/feature that may be derived from variations resulting from a stack up (i.e., the sum) of a multiplicity of such individual tolerances.

Any use of a friction fit (i.e., an interface fit) between two mating parts described herein indicates that the opening (e.g., a hole) is smaller than the part received therein (e.g., a shaft), which may be a slight interference in one embodiment in the range of 0.0001 inches to 0.0003 inches, or an interference of 0.0003 inches to 0.0007 inches in another embodiment, or an interference of 0.0007 inches to 0.0010 inches in yet another embodiment, or a combination of such ranges. Other values for the interference may also be used in different configurations (see e.g., "Press Fit Engineering and Design Calculator," available at: www.engineersedge.com/calculators/machine-design/press-fit/press-fit-calculator.htm).

Any described use of a clearance lit indicates that the opening (e.g., a hole) is larger than the part received therein (e.g., a shaft), enabling the two parts to move (e.g. to slide and/or rotate) when assembled, where the gap between the opening and the part may depend upon the size of the part and the type of clearance fit—i.e., loose running, free running, easy running, close running, and sliding (e.g., for a 0.1250 inch shaft diameter the opening may be 0.1285 inches for a close running fit, and may be 0.1360 inches for a free running fit; for a 0.5000 inch diameter shaft the opening may be 0.5156 inches for a close running fit and may be 0.5312 inches for a free running fit). Other clearance amounts are used for other clearance types. See "Engineering Fit" at: https://en.wikipedia.org/wiki/Engineering_fit; and "Three General Types of Fit," available at www.mm-to.org/dclark%Reports/Encoder%20Upgrade/tittolerences%20%5BRead-Only %5D.pdf.

FIG. 1 shows a first embodiment of the dental implant organizer case 10 of the present invention, which serves to organize the multitude of implant platforms that may need to be readily available to an oral surgeon during the performance of implant procedures. As seen in FIG. 2, the dental implant organizer case 10 may comprise an elongated left-side case portion 10L being pivotally and/or releasably attached to an elongated right-side case portion 10R using hinge 110, where the left-side case portion and the right-side case portion may pivot 180 degrees relative to each other. Hinge 110, and its attachment to both the elongated left-side case 10L and the elongated right-side case 10R may permit the two cases to pivot between a collapsed position, in which they are parallel but side-by-side with each other (FIG. 1), and an extended position, in which they are parallel but in line with each other (FIG. 2). The left-side case 10L and the right-side case 10R may be releasably secured to remain in the collapsed position, by using, on the case ends opposite from the hinge 110, a twist lock and pivotable plate, similar to the arrangement in U.S. Pat. No. 3,407,454 to Myatt for "Quick Release Fasteners." the disclosures of which are incorporated herein by reference.

Either the left-side case 10L or the right-side case 10R may include a handle that is centrally positioned, and which may be pivotally attached to the case to be able to pivot down and out of the way during a procedure or when storing the organizer case 10, or be able to pivot upwards to be grasped by the practitioner for transporting of the dental implant organizer case 10. Alternatively, a separate handle 25L may be pivotally secured to the left-side case 10L and a separate handle 25R may be pivotally secured to the right-side case 10R of implant organizer case 10. The two handles 25L and 25R may snap together when the case is in the collapsed position, through the use of a post member 25P on one handle, with the post member being received in a recess in the other handle using a friction fit.

Both the left-side case 10L and the right-side case 10R of implant organizer case 10 may include a housing that may be segregated using a plurality of walls (or a single integral multi-flanged feature) to form a series of compartments. Since the prosthodontic surgeon will generally not implant a platform within the upper or lower jaw bone at the site of the wisdom teeth (teeth numbers 1, 16, 17, and 32), both the left-side case 10L and the right-side case 10R of implant organizer case 10 may preferably have seven compartments each, which may be accessible from the top of the case. Left-side case 10L may comprise compartments C2, C3, C4, C5, C6, C7, and C8, for those corresponding tooth numbers, and right-side case 10R may comprise compartments C9, C10, C11, C12, C13, C14, and C15.

Each of these compartments may be adapted to support one or more implant platform vials. To accommodate a "suggested" implant platform size (diameter and length) for a particular site (tooth location), and at least two other platform sizes that may possibly be needed by the surgeon as an alternative (indicated graphically in the figures as 1°, 2°, and 3° platform selections), each of the compartments may include a support member configured to support at least one such vial, and may preferably be configured to support three such vials—vials 100V, 101V, and 102V. Support for a fourth or a fifth alternate vial or even more alternate vials could be similarly accommodated using the support means discussed hereinafter.

Since these vials are typically cylindrical (see FIG. 1), each of the compartments may comprise hollow cylindrical holder members that may protrude upwards from its bottom wall. As seen for the example compartment C2 in FIG. 2C, to support three cylindrical vials, the compartment may have three hallow cylinders. $C2i$, $C2ii$, and $C2iii$ therein. These hollow cylinders may be integrally formed with the compartment's bottom wall, or may alternatively be secured to the bottom wall using any suitable manufacturing method, including, but not limited to, using mechanical fasteners through a flange extending from the cylinder, using an adhesive, by friction welding, etc. The holder member need not be cylindrical, and could alternatively have a square-shaped cross-section to support a cylindrically shaped vial, or a rectangular-shaped vial. For any shaped holder member being used, it may preferably be slightly oversized to provide some clearance with the vial to account for differences in the size of packaging used by various platform manufacturers. In addition, rather than using a form-fitting support member that generally mirrors the cross-sectional shape of the packaging of the platform, vial support may alternatively be provided by a series of wires (3 or more wires), each of which may protrude upwardly from the bottom wall of the compartment, and which may be bent by the oral surgeon or his/her assistant to suitably support the vial's uniquely shaped envelope.

Figure 2A:
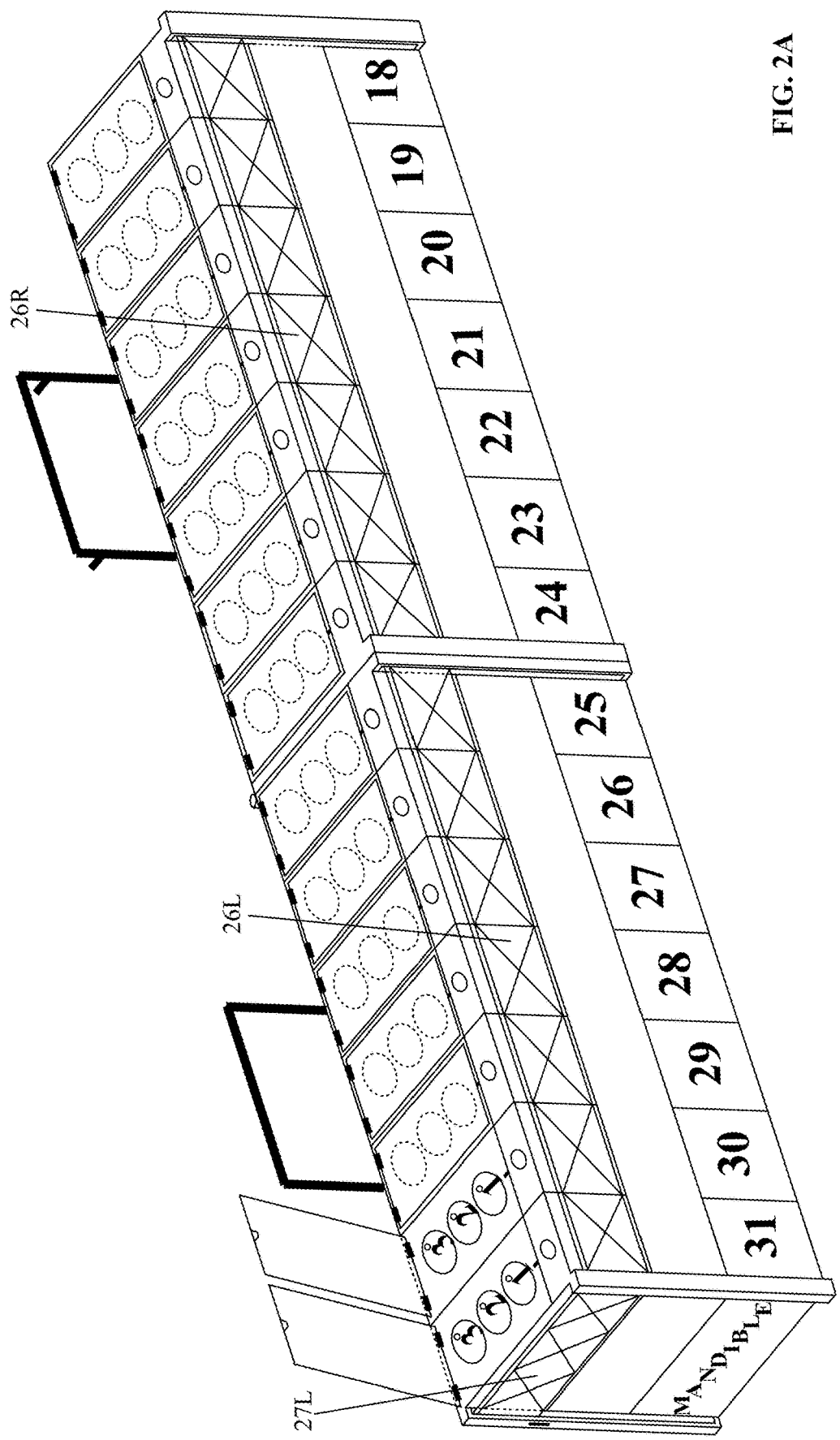
FIG. 2A is the dental implant platform organizer case of FIG. 2, being shown in the extended, in-line position for use during an implant procedure, and with its slidable shields having been slid upward to conceal the maxilla tooth numbers during a procedure requiring implants on the patient's mandible.
Figure 2B:
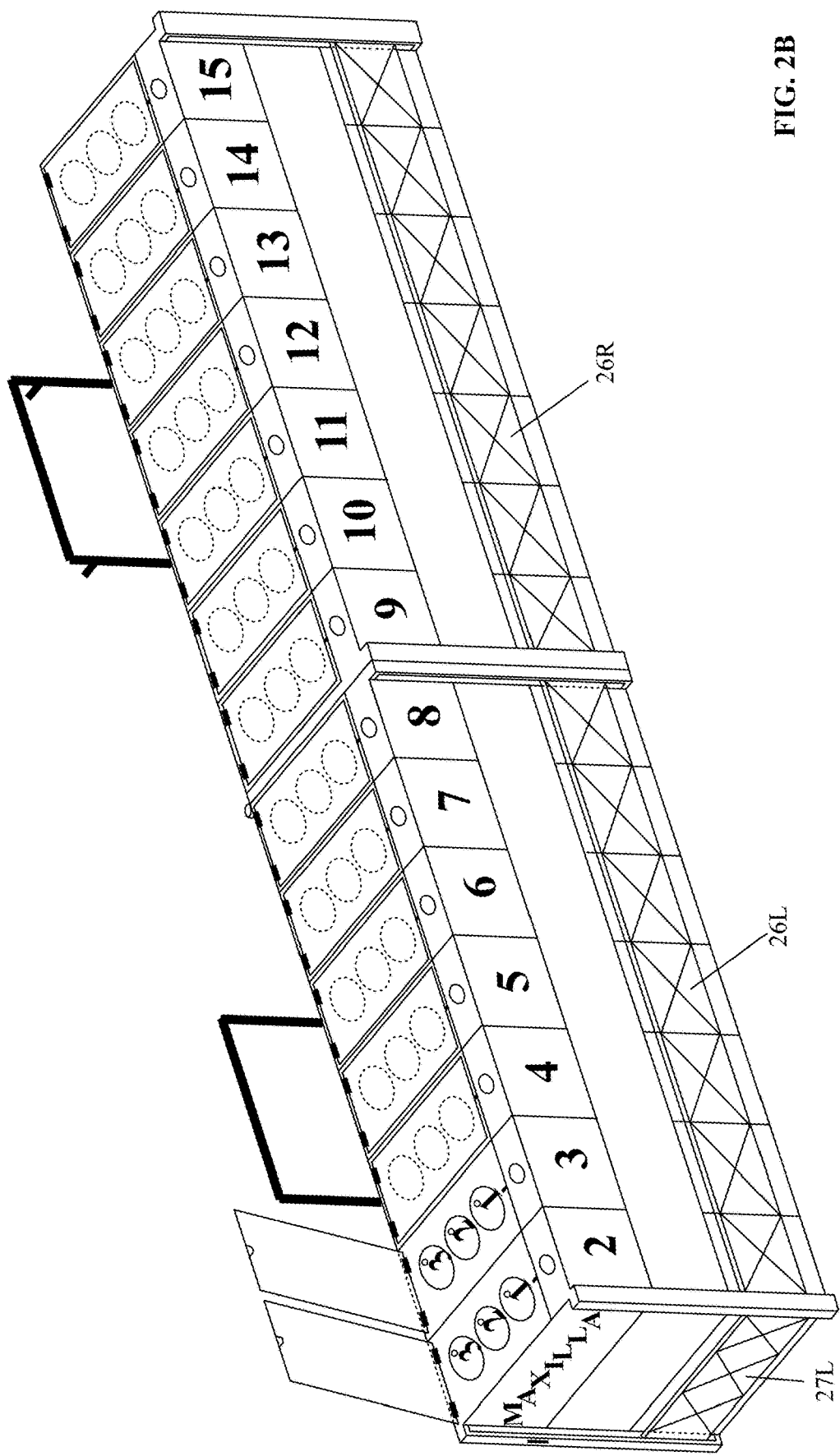
FIG. 2B is the dental implant platform organizer case of FIG. 2, being shown in the extended, in-line position for use during an implant procedure, and with its slidable shields having been slid downward to conceal the mandible tooth numbers during a procedure requiring implants on the patient's maxilla.
Figure 2D:
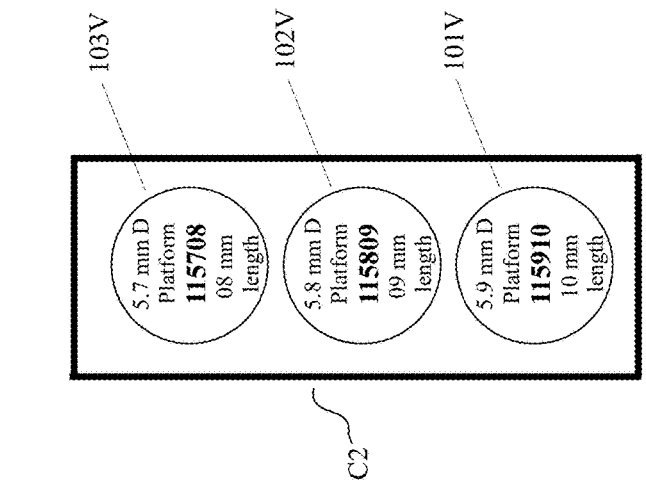
FIG. 2D is a top view of the compartment of FIG. 2C.
Figure 2C:
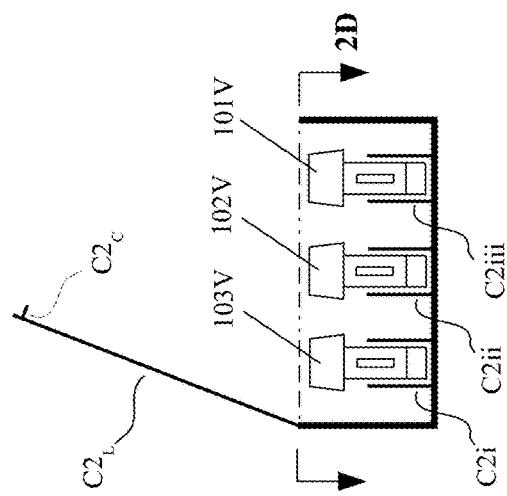
FIG. 2C is a side cross-sectional view of a compartment of the case of FIG. 2B, and is shown having support for three implant platform vials, which are shown stored therein.
Figure 2F:
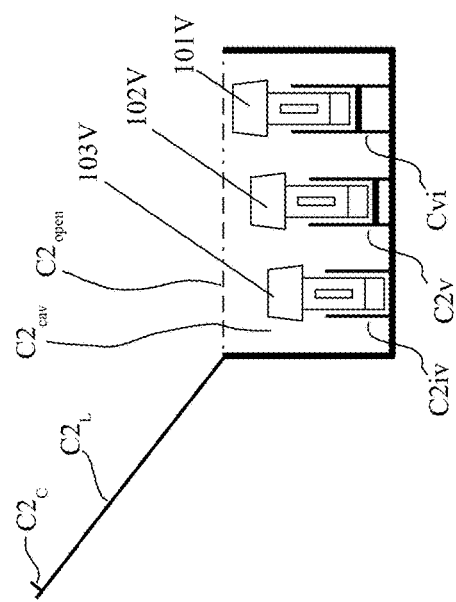
FIG. 2F is the side cross-sectional view of FIG. 2C, but showing a multi-level support member for the implant platform vials.

Each of the alternative holder members described herein may preferably be configured to releasably receive and support one or more implant platform vials in an upright position, as seen in the cross-sectional view of FIG. 2C, because the vials typically have its identifying characteristics labeled upon its top cover, as seen in FIG. 2D. This permits the oral surgeon to glance at the label and verify that the vial containing the proper sized platform is being removed for use at a particular implant site. This upright positioning and suitable spacing between the vials when stored within a compartment also permits the practitioner, or an assistant, to easily grasp and remove the desired vial therefrom. Also, as depicted in FIG. 2C and FIG. 2D, the support provided for the dental implant vials may be such that they may be positioned in-line within the elongated compartment. Also, as seen in FIG. 2F for the three hallow cylinders, $C2iv$, $C2v$, and $C2vi$ therein, the vials may be stored in the upright position at different levels, so that the vial with the preferred implant platform is most easily accessible, the first alternate platform is next most accessible, and so on, which may serve as a visual reminder as to the size preferences.

Figure 1A:
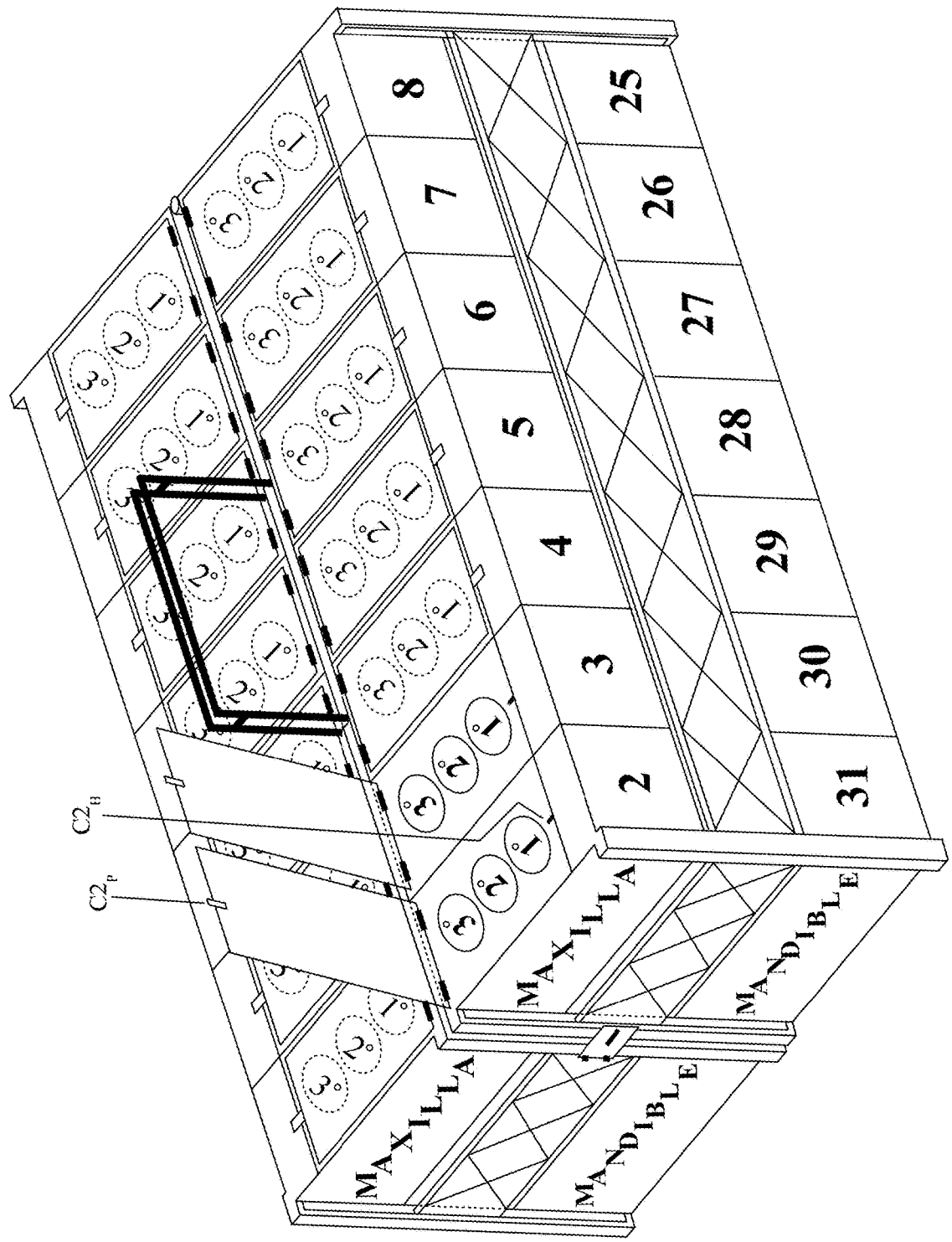
FIG. 1A is the organizer case of FIG. 1, but is shown using a hook material and a loop material for releasably securing of each of the lids in the closed position.
Figure 1B:
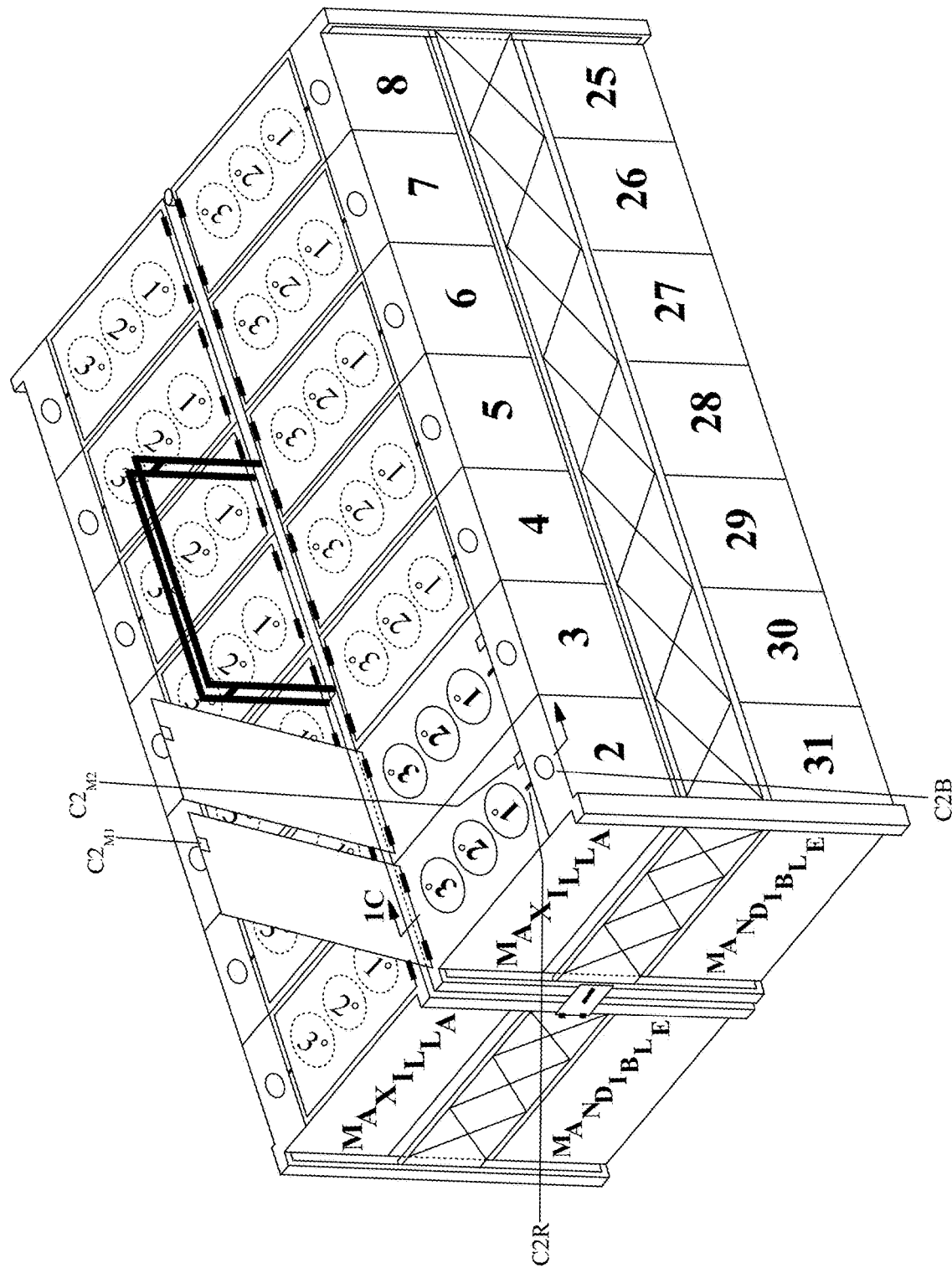
FIG. 1B is the organizer case of FIG. 1, but shown using a first magnet and a second magnet for releasably securing of each of the lids in the closed position.
Figure 1C:
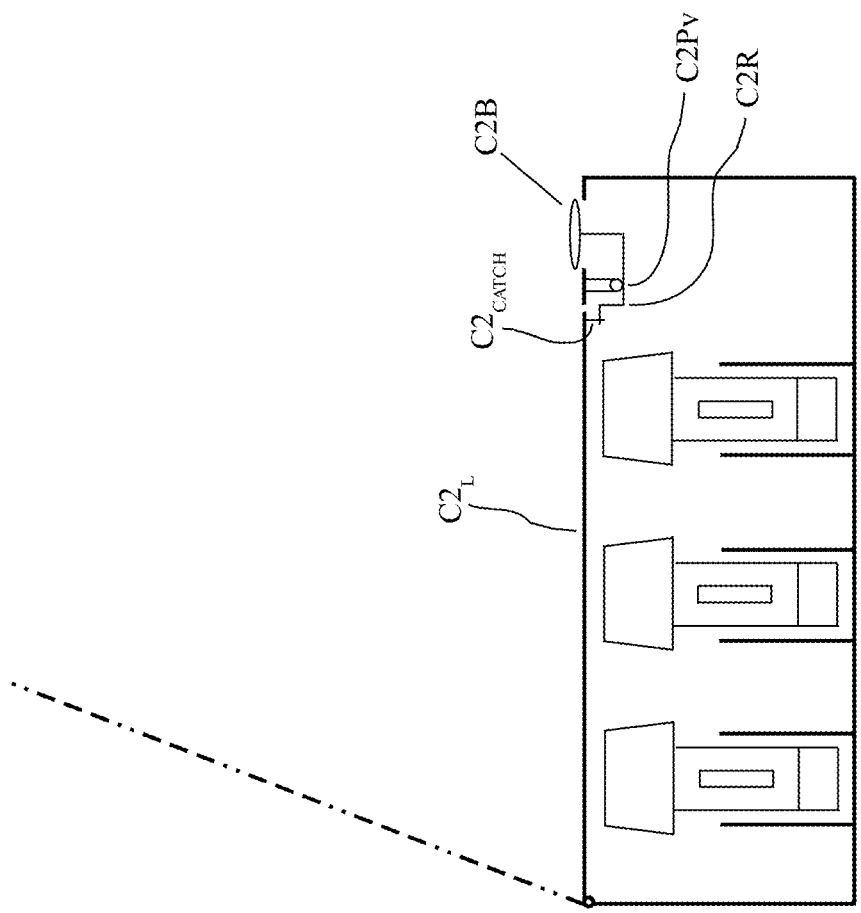
FIG. 1C is a side cross-sectional view showing the rocker arm and the push button for one of the compartments of the organizer case, as seen in the perspective view of FIG. 1B.
Figure 1D:
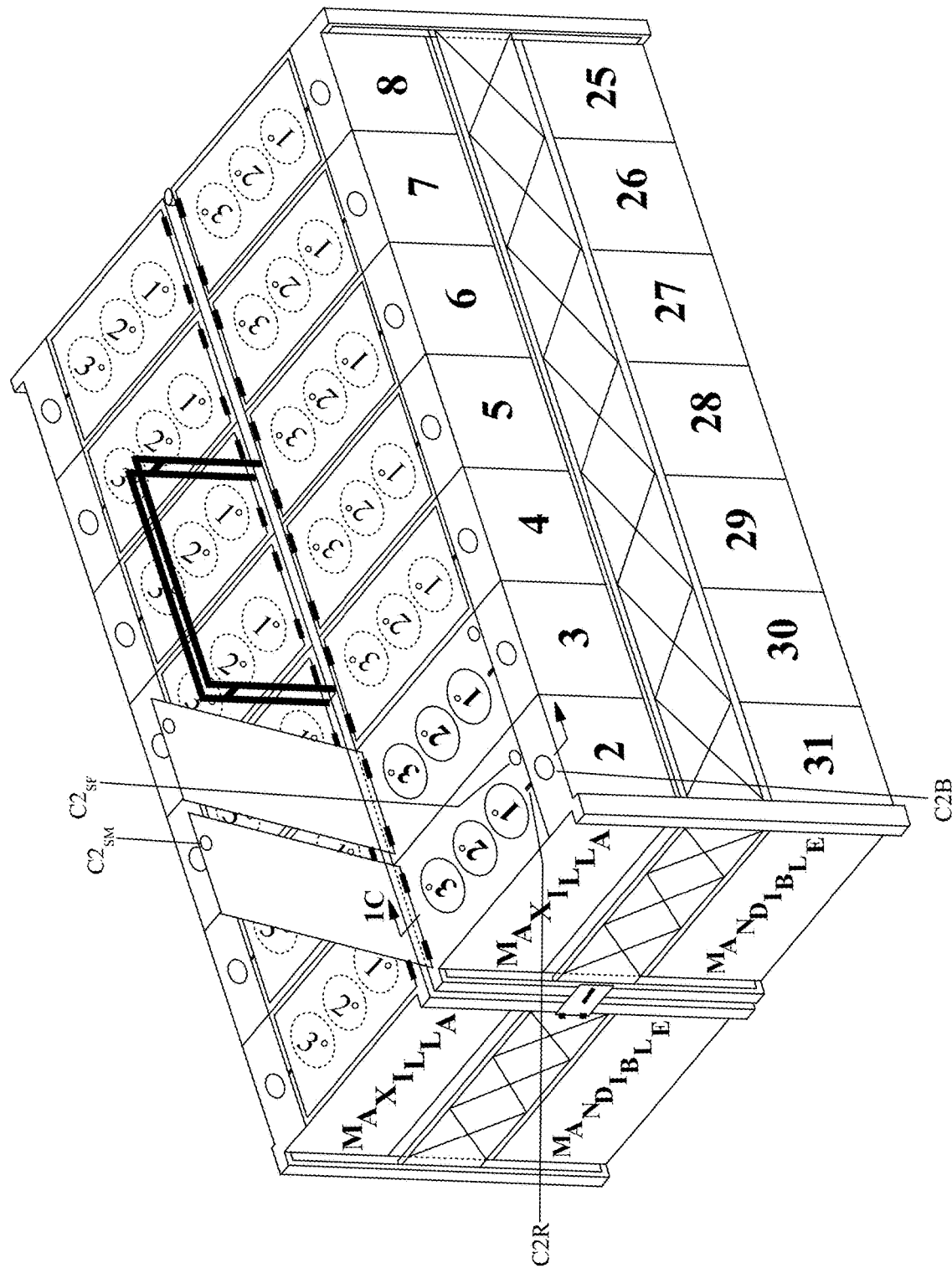
FIG. 1D is the dental implant platform organizer case of FIG. 1, but which further includes a male snap and a female snap that form a snap fastener that may be usable to releasably secure the lid in a closed position.

Each compartment may preferably also have a hinged lid—lid C2L for the compartment C2 in FIG. 2C. The lid may pivot about a hinge that may have a torsion spring (e.g., spring $C2_T$ in FIG. 2), compression spring, or other biasing means thereon that serves to bias the lid from a closed position, in which it retains the vials within the compartment, into an open position, which exposes an opening $C2_{open}$ into a cavity $C2_{cav}$ of the compartment (see FIG. 2F). With the lid in the open position, the oral surgeon may freely access any one of the vials for implantation of the platform contained therein. The hinged lid may be retained in the closed position by any suitable latching means. For example, latching of the lid may be accomplished using a hook and loop fastening fabrics (e.g., hook material $C2_H$ and loop material $C2_P$ for compartment 2 shown in FIG. 1A), which is known by the trade name Velcro®, where a strip or tab of the material may extend beyond the lid to be graspable by the person seeking to separate the hook and loop fabric pieces and open the cover member. The latching of the lid may also be through the use of a snap fastener (e.g., male snap $C2_{SM}$ on the cover of the second compartment, and female snap $C2_{SF}$ on a portion of the framework shown in FIG. 1D), such as the "Fastening Snap" of U.S. Pat. No. 3,975,803 to Katayama, the disclosures of which are incorporated herein by reference. As another example, the lid may have a small magnet on a bottom surface that could overcome the biasing through attraction to a corresponding magnet that is mounted within the compartment or is inset into the frame that supports the lid (e.g., magnet $C2_{M1}$ on the cover of the second compartment, and magnet $C2_{M2}$ on a portion of the framework shown in FIG. 1B). A rocker arm $C2_R$ may be pivotally attached at C2PV to the framework that supports the compartment, and may have one end that is connected to a push-button C2B, with the other end being capable of engaging and driving the lid C2L, to thereby separate the magnets, and allow the torsion spring to bias the lid into the open position. The magnet/release arrangement may also be the same as shown by U.S. Pat. No. 4,026,588 to Bisbing for "Push-to-Open Magnetic Catch," the disclosures of which are incorporated herein by reference. Alternatively, instead of a magnet, a mechanical catch $C2_C$ on the lid $C2_L$ may engage the rocker arm, and which may become disengaged therefrom by a user depressing the button $C2_B$ when seeking to open the lid. Rather than a rocker arm, a simple, spring biased, siding member or members may be used to engage the catch on the lid, similar to the latch on a door or on the glove box of a car. As another alternative, the push-to-open arrangement for each of the lids may be the integrally molded plastic hinge disclosed by U.S. Pat. No. 7,497,351 to Amundson for "Wet Wipe Dispensing System."

A lid may only be opened by a practitioner during a procedure for tooth/teeth numbers for which an implant is being placed during the surgery. Each lid may be opaque, or may alternatively be translucent to permit the practitioner or an assistant of the practitioner to recognize that an implant within the case has been utilized for a previous procedure, and that it needs to be replaced before using the case for another procedure.

The upper front of the left-side case 10L may have a placard 151 (or have numbers stenciled thereon), to indicate tooth numbers for respective compartments for the teeth of a patients upper right side, which, in the American system, would principally be teeth numbers: 2, 3, 4, 5, 6, 7, and 8 (wisdom tooth #1 not being included). In the European system (Palmer Notation method) they would be teeth numbers: (UR) 7, 6, 5, 4, 3, 2, and 1. The upper front of the right-side case 10R may have a placard 153 (or have numbers stenciled thereon), to indicate the tooth numbers for respective compartments for the teeth of a patient's upper left side, which, in the American system, would principally be teeth numbers: 9, 10, 11, 12, 13, 14, and 15 (UL 1, 2, 3, 4, 5, 6, and 7 in the European system).

In addition, the lower front of the left-side case 101, may have a placard 152 (or have numbers stenciled thereon), to indicate the tooth numbers for the teeth of a patient's lower right side, being teeth numbers: 31, 30, 29, 28, 27, 26, and 25 (LR7-1 in the European system). Finally, the lower front of the right-side case 10R may have a placard 154 (or have numbers stenciled thereon), to indicate the tooth numbers for the teeth of a patient's lower left side, being teeth numbers: 24, 23, 22, 21, 20, 19, and 18 (LL 1-7 in the European system).

A shield 27L may be slidably received on the front of the left-side case 10L, by having the ends of the shield be received in a friction fit in a vertical recess at the first end 10Li and at the second end 10Lii of the left-side case. A shield 27R may similarly be received on the front of the right-side case 10R, by having the shield be slidably received on the front of the case, by having the ends of the shield be received in a friction fit in a vertical recess at the first end 10Ri and at the second end 10Rii of the right-side case. The shields 27L and 27R may thus be slid upward to conceal the teeth numbering for the maxilla, when the case is being used for implants on the patient's mandible (FIG. 2A), or shields 27L and 27R may instead be slid downward to conceal the teeth numbering for the mandible, when the case is being used for implants on the patient's maxilla (FIG. 2B). A placard or stenciling may also appear on the sides of the case identifying the upper numbering as being for the "MAXILLA," while the another placard or stenciling may identify the lower numbering as being for the "MANDIBLE." A slidable shield 27L, located on the first end 10Li of left-side case 10L may be used to similarly conceal the "MAXILLA" stencil when the case is being used for placing implants within the mandible, or vice versa, and a slidable shield 27R, located on the first end 10Ri of right-side case 10R may be used to correspondingly conceal the "MAXILLA" and "MANDIBLE" lettering thereon.

Figure 2E:
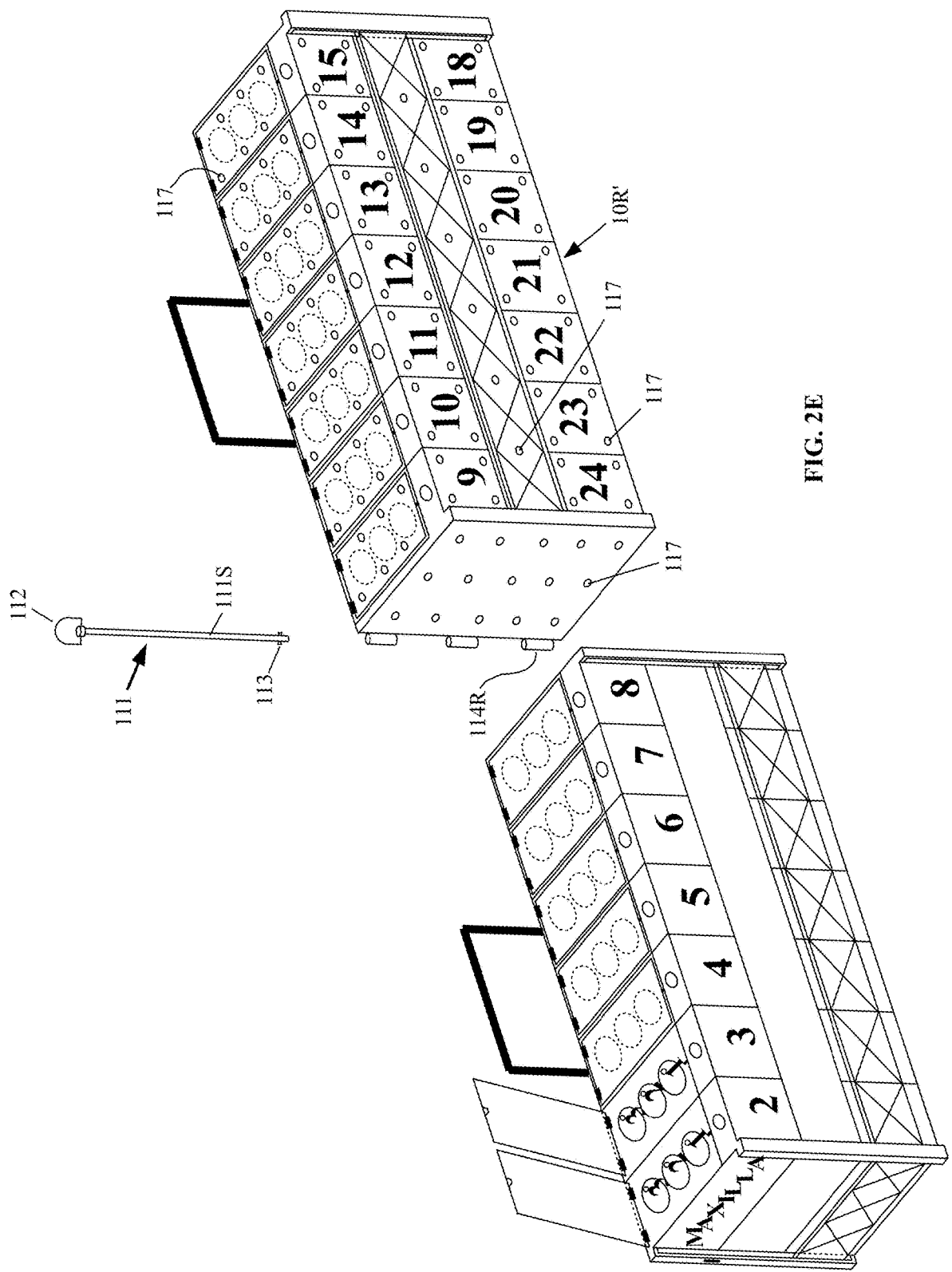
FIG. 2E is an exploded view of the organizer case of FIG. 2.

FIG. 2E is an exploded view that illustrates a couple of different variations of the dental implant organizer case 10. First, the organizer case shown in FIG. 2F, may be configured to permit complete separation of the left-side case portion from the right-side case portion. Rather than using the simple hinge pin 110 shown in the previous figures, a hinge pin 111 may instead be used, which may include a ring 112 secured to the head of the pin. In addition, the bottom portion of the hinge pin 111 may include a detent 113. The detent 113 may comprise a pair of opposingly biased spherical balls being retained within a transverse orifice in the shaft 111S of the hinge pin 111, which, once passed through the barrel sections 114R of the right-side case section and through the barrel sections of the left-side case section, are biased outwardly to releasably secure the hinge pin relative to the lowermost barrel section. Additionally, although it is only shown on the right-side case portion 10R', both case portions (left and right) may include a plurality of openings 117, that may be in the sides and back of the case, as well as in the lids of the compartments, and in the shields, to permit penetration therethrough by steam and pressure within an autoclave, to provide for sterilization of the case-portions. Being able to separate the left-side case portion from the right-side case portion, by withdrawing the hinge pin 111 from the barrel sections using the ring 112, better facilitates fitting the organizer case into an office-sized autoclave for sterilization. It should be noted that both the left and right-side case portions with the plurality of openings therein may also be subjected to cold sterilization, which may be per U.S. Pat. No. 4,839,004 to Castellini for "Method and Apparatus for Cold Sterilization of Surgical Instruments, in Particular Dental Surgery Instruments." the disclosures of which are incorporated herein by reference.

Figure 3:
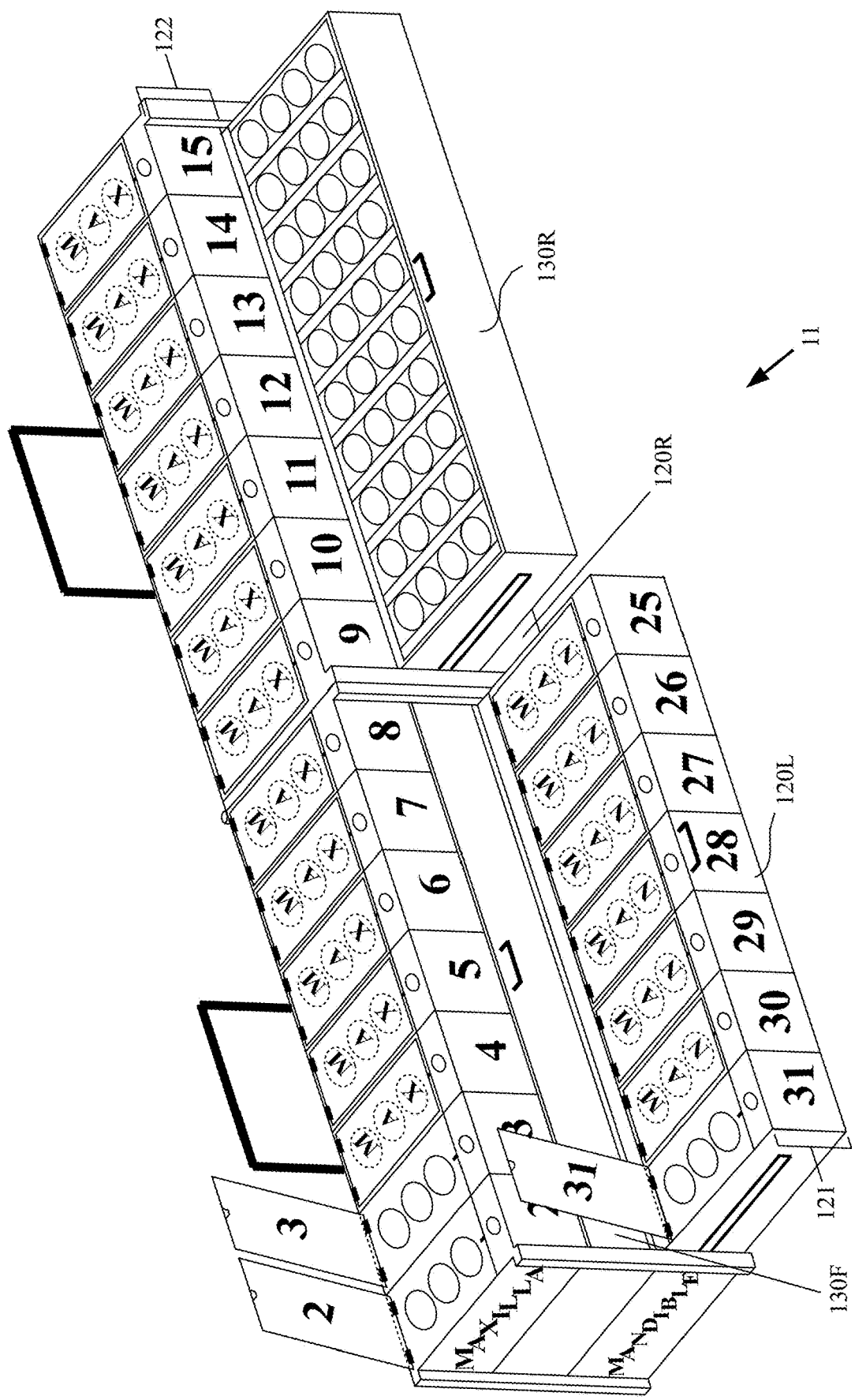
FIG. 3 shows a variation to the dental implant platform organizer case of FIG. 1, and may include a lower set of compartments within a pair of slidable trays, for use during an implant procedure requiring implants on both the patient's maxilla and mandible.

FIG. 3 illustrates another variation of case 10, in the form of dental implant organizer case 11, which may generally be constructed the same as organizer 10, except that the left-side case 10L and the right-side case 10R may each have a respective lower tray, 120L and 120R, which may slide outwardly from the frame. Each lower tray 120L and 120R may also contain seven in-line compartments that may preferably support a number of vials comparable to what is supported by the upper compartments. Therefore, in this embodiment, the upper level of compartments 122, which include the upper left compartments (C2, C3, C4, C5, C6, C7, and C8) and the upper right compartments (C9, C10, C11, C12, C13, C14, and C15) may be dedicated to only organizing/storing vials of implant platforms for the teeth of the maxilla. Also, the lower level of compartments 121, which include corresponding lower compartments (C31, C30, C29, C28, C27, C26, C25, C24, C23, C22, C21, C20, C19, and C18) of the lower trays (120L and 120R) may be dedicated to only organizing/storing vials of implant platforms for the teeth of the mandible. Note that rather than using a slidable tray, the housing for this embodiment may simply be stepped, so that both the upper and lower compartments may simultaneously be exposed all of the time.

In addition, the dental implant organizer case 11, since it may not require the shields utilized with organizer 10, may instead have a center tray 130L on the left-side case 10L and a center tray 130R on the right-side case 10R, with each center tray being slidably received between the upper compartments and the lower tray. Center trays 130L and 130R may have support therein for receiving a closely packed plurality of vials that may be used as replacements for the vials organized and presented within the upper and lower compartments, after they have been used in a procedure. Each slidable center tray may have a protruding handle, or an inset handle. The drawer slides that are used to permit the center trays to slide outwardly may have a detent, in order to normally retain the trays in the closed position.

Stenciling may be provided on the top of the lids for the upper compartment (abbreviated as "MAX") to identify their use for implantation on the maxilla, and for the lower compartments (abbreviated as "MAN") to identify their use for implantation on the mandible. The "MAX" and "MAN" stenciling may serve as an added reminder for the oral surgeon, as to the intended location for those implants (maxilla or mandible), and the tooth number may also be stenciled on the bottoms of the lids for the same reason.

Prior to performing an extensive implant procedure, the oral surgeon or assistant may position the case on a cart in proximity to the surgical chair, and pivot the left-side and right-side cases into the extended, in-line position. The lower trays may then be slid outwardly to expose the lower compartments. To further assist the surgeon during the procedure, the lids of only the tooth locations to receive implants may be unlatched, thereby biasing the lids into the open position. The surgeon will therefore have the correct assortment of tooth-specific implant platforms readily available to him/her during the procedure, along with a textual indication of which implant locations—tooth numbers and jaw position (maxilla/mandible)—that those platforms are intended for, to serve as a visual cue during the procedure to eliminate confusion and to help prevent accidental misplacement of an implant.

Figure 4:
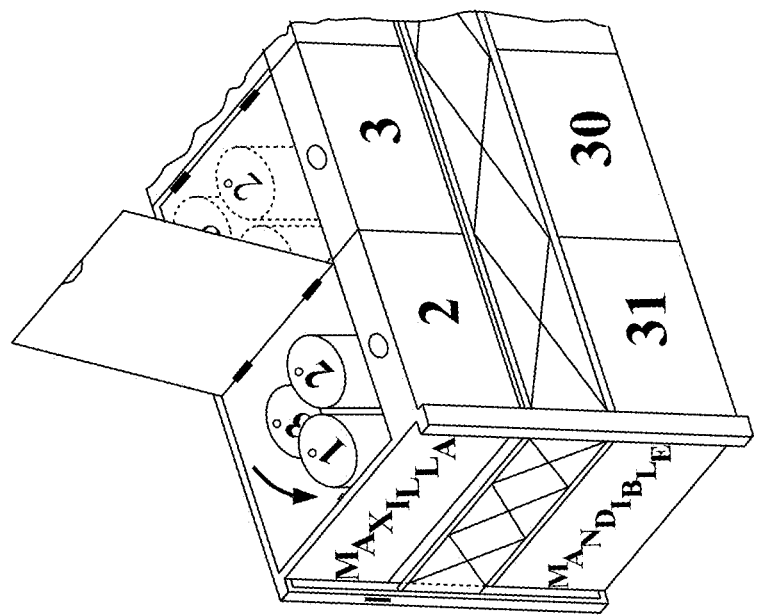
FIG. 4 shows another variation to the dental implant platform organizer case of FIG. 1, and may have the three alternative implant platforms for each tooth location releasably received within a receptacle, with the three receptacles being rotatably mounted upon a lazy Susan.

FIG. 4 shows an alternative vial holder arrangement within the compartments, whereby the holder members for the vials may be arranged in a circular pattern, and may be supported upon a rotatable plate, like a lazy Susan. In addition, the holder member for the vial containing the "suggested" implant size, and the holder members for the vials containing the second and third implant platform choices, may be adapted to provide different upwardly protruding heights for the different vials, such that the "suggested" implant platform protrudes upwardly the most, then the second choice would protrude upwardly the next highest, with the third choice being disposed at the lowest height above the compartment floor. It should also be noted, that for any of the organizer cases disclosed herein, the lids may pivot in any desired direction, including sideways, as illustrated in FIG. 4.

FIG. 5 illustrates an alternative organizer case embodiment of the current invention, in the form of dental implant organizer case 12. Dental implant organizer case 12 may have a series of compartments set in a semi-circular arrangement, being oriented similar to the way the teeth in a patient's mouth appear to the oral surgeon. Dental implant organizer case 12 may contain shields 226L, 226C, and 226R (FIG. 6), similar to those used on organizer case 10. These shields may slide upward or downward, depending upon whether the case is to be used for implants on either the Maxilla or the Mandible. Alternatively, shields 226L, 226C, and 226R may be eliminated and the semi-circular dental implant organizer case may have two sets of compartments similar to organizer case 11.

Figure 7A:
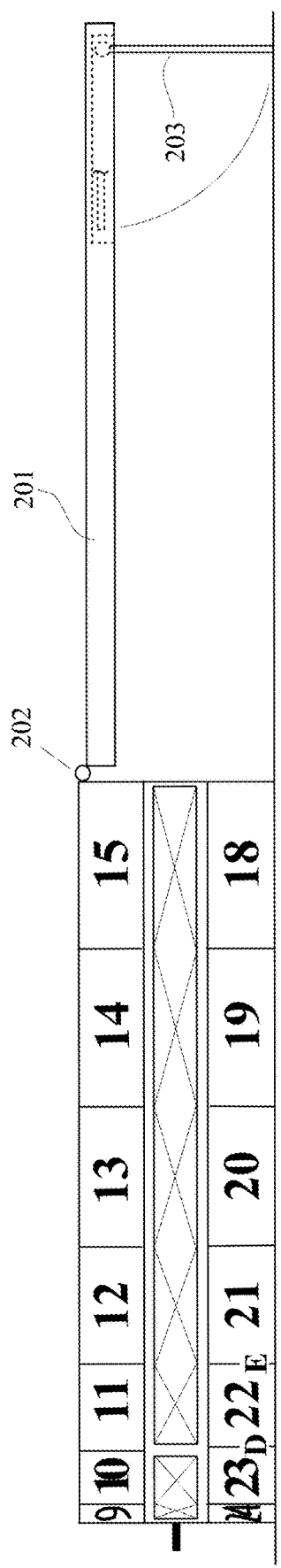
FIG. 7A is a side view of the organizer case of FIG. 5, with the cover shown in the open position.
Figure 7B:
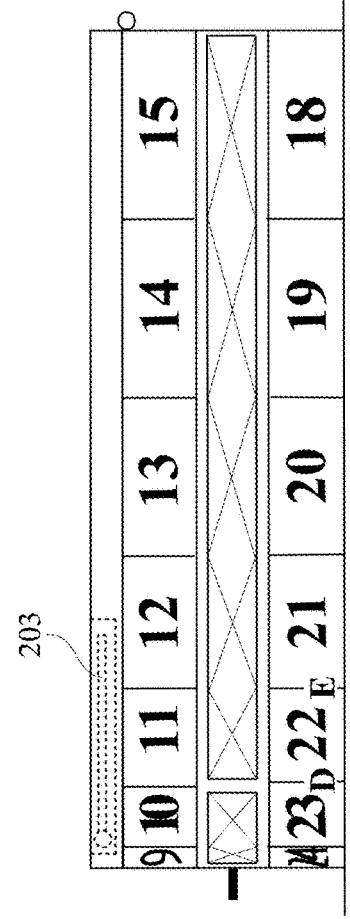
FIG. 7B is the side view of FIG. 7A, but with the cover shown in the closed position.

A case cover 201 may be pivotally attached to the case using hinge(s) 202. The underside of the cover 201 may have one or more placards 250, which may be visible to the oral surgeon during a procedure when the case is opened, and which may provide procedural guidelines and reminders. The interior central portion of the case may be left open to be usable for storage. The cover may be supported in the open position to be generally parallel with the surface upon which the case rests, through the use of stops on the hinge(s) 201 to limit pivotal movement of the cover, or through the use of a support leg 203. The support leg 203 may rotate 90 degrees into an extended position to provide support for cover 201 when the cover is opened, as seen in FIG. 7A, and it may thereafter counter-rotate 90 degrees to return to a retracted position where it is retained within a recess in cover 201, when the cover is closed, as seen in FIG. 7B. In addition to, or as an alternative to, the cover 201, each of the compartments may have a lid pivotally attached to the case to selectively provide access to each compartment, similar to what was illustrated for organizer case 11.

Dental implant organizer case 12 may include a plurality of openings in the sides and back of the case, as well as in the cover and/or lids of the compartments and in the shields, similar to case 10R' in FIG. 2E, so that case 12 may also be subjected to sterilization in an autoclave or to cold sterilization.

Figure 8A:
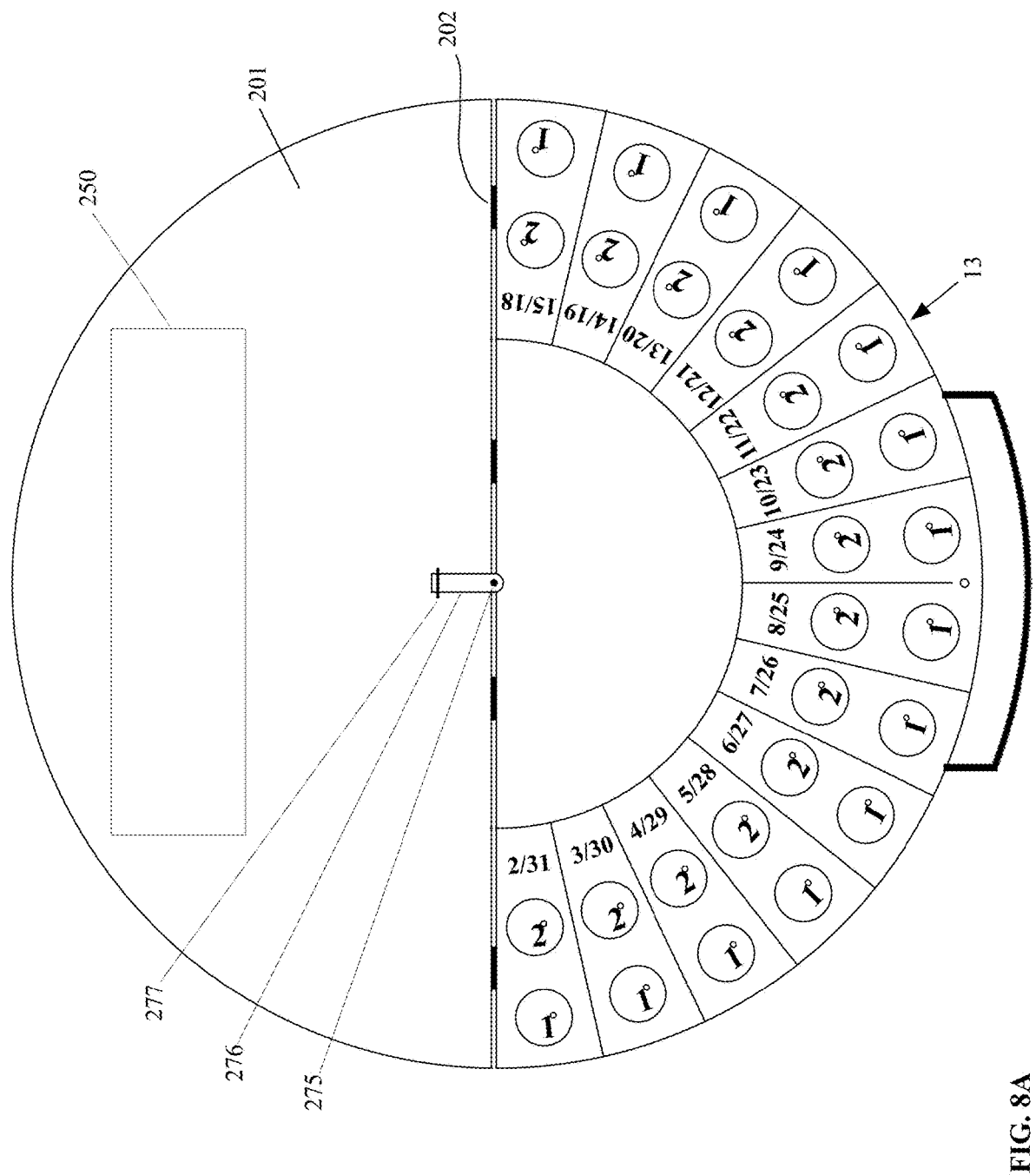
FIG. 8A illustrates a variation of the organizer case of FIG. 5, which provides support for one or more rotator shields that provide selective access to the compartments containing implants for the tooth locations for a particular procedure.

A variation of the semi-circular implant organizer case 12 is shown by organizer case 13 that is shown in FIG. 8A. Organizer case 13 may additionally include a pin 275 that may be usable to pivotally receive rotator shields that may serve to provide selective access to the compartments containing implants for the tooth locations for a particular procedure. The pin 275 may be appropriately secured to the case using any suitable means. The pin 275 may be secured to a strap 276, which may be made of a rigid or flexible material. The strap 276 may be stitched to or hinged to the inside of the cover 201 at 277 to allow the pin to drop into the central storage area when the cover is closed and the case is not in use, or alternatively to allow the pin to be positioned proximate to the center of the semi-circular case when the cover is opened. Where the strap 276 is flexible, stitching may preferably be used at location 277, and where the strap 276 is made of a rigid material, a hinge arrangement at 277 may preferably be used.

Figure 8B:
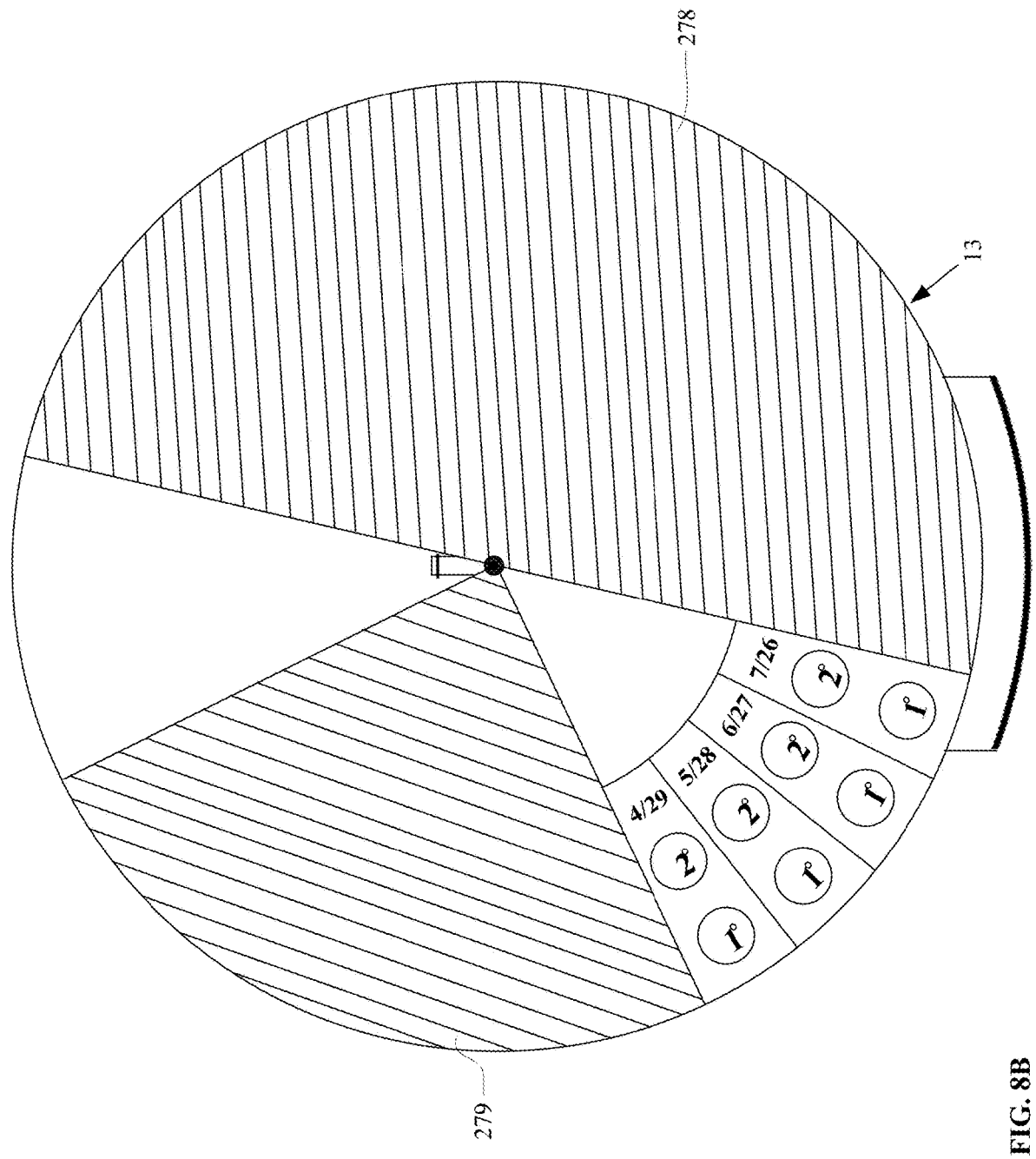
FIG. 8B shows the organizer case of FIG. 8A, with two rotator shields that have been received thereon to only permit access to the compartments for teeth numbers 4/29, 5/28, 6/27, and 7/26.

A couple of examples of the rotator shields usable with this embodiment are illustrated in FIGS. 8C, 8D, and 8E. Rotator shield 278 may be a semi-circular shield member that may have a ring 278R secured thereto to be proximate to a center point of the semi-circle. Rotator shield 279 may be constructed to form one-fourth of a circle, and may have a ring or a snap 279S secured thereto to be proximate to a center point of the quarter-circle. The snap may be, for example, the snap member of U.S. Pat. No. 3,975,803 to Katayama. Use of these example shields is illustrated in FIG. 8B. The ring 278R of shield 278 may be received upon the pin 275 to be pivotable thereon. Similarly, where shield 279 comprises a ring, it too may be received upon the pin to be pivotable thereon. Where the snap is used instead of the ring, the snap 279S on shield 279 may be used to releasably secure the shield to the tip of the pin 275 to be rotatable thereon. Use of the snap may also serve to releasably retain any number of pivotable shields upon the pin to better facilitate their pivotal movement, as follows.

The rotator shields may be pivoted to selectively provide access to only those compartments that the oral surgeon will need during a procedure, to avoid errantly utilizing the wrong implant platform at a particular site. For example, where the oral surgeon may be installing platforms at the number 4, 5, 6, and 7 teeth of the Maxilla, The rotator shield 278 and the rotator shield 279 may be positioned as seen in FIG. 8B, so that only those implant platforms will be visible to, and available for the oral surgeon, during the procedure. Small magnets, for example, the magnets 279M on rotator shield 279 seen in FIG. 8E, may be used prevent inadvertent rotation of the rotator shields, once they have been set for the surgery, by their attraction to corresponding magnets on the upper periphery of the case. Where the oral surgeon needs to only implant a platform at a patient's tooth numbers 4, 5, and 7, but not at tooth number 6, the rotator shield 280 seen in FIG. 8E may also be used to block access to the number "6/27" compartment. Rotator shield 280 may thus sweep out an arc segment that is $1/14^{th}$ of a semi-circle to thereby block access to only a single compartment. Other rotators shields may also be conveniently utilized, such as a rotator shield that sweeps out $1/7^{th}$ of a semi-circle, to thereby block access to two adjacent compartments, and/or a rotator shield that sweeps out $3/14^{th}$ of a semi-circle, to thereby block access to three adjacent compartments, etc. The rotator shields may be stacked upon each other using the pin 275.

FIGS. 9-11 illustrate a front, end, and top view of a multi-purpose rack 300 that may be used to organize a plurality of containers (with and/or without "intermediate packaging") each of which hold a dental implant platform for a particular tooth, to assist a surgeon during dental implant surgery, and which rack may also be separated for a portion thereof to be used during a restorative procedure for dental implants. It is noted that each dental implant container holds one implant, and is itself usually shrouded in plastic and cardboard (i.e., intermediate packaging), and a plurality of such packaged dental implant containers are grouped together in a box or other outer packing material for shipment.

The rack 300 may be formed of either one part (i.e., only upper portion 310), or may be formed of two component parts that may be releasably secured together, as shown in FIGS. 12-13 (i.e., the upper portion 310 and a base portion 350).

Figure 19:
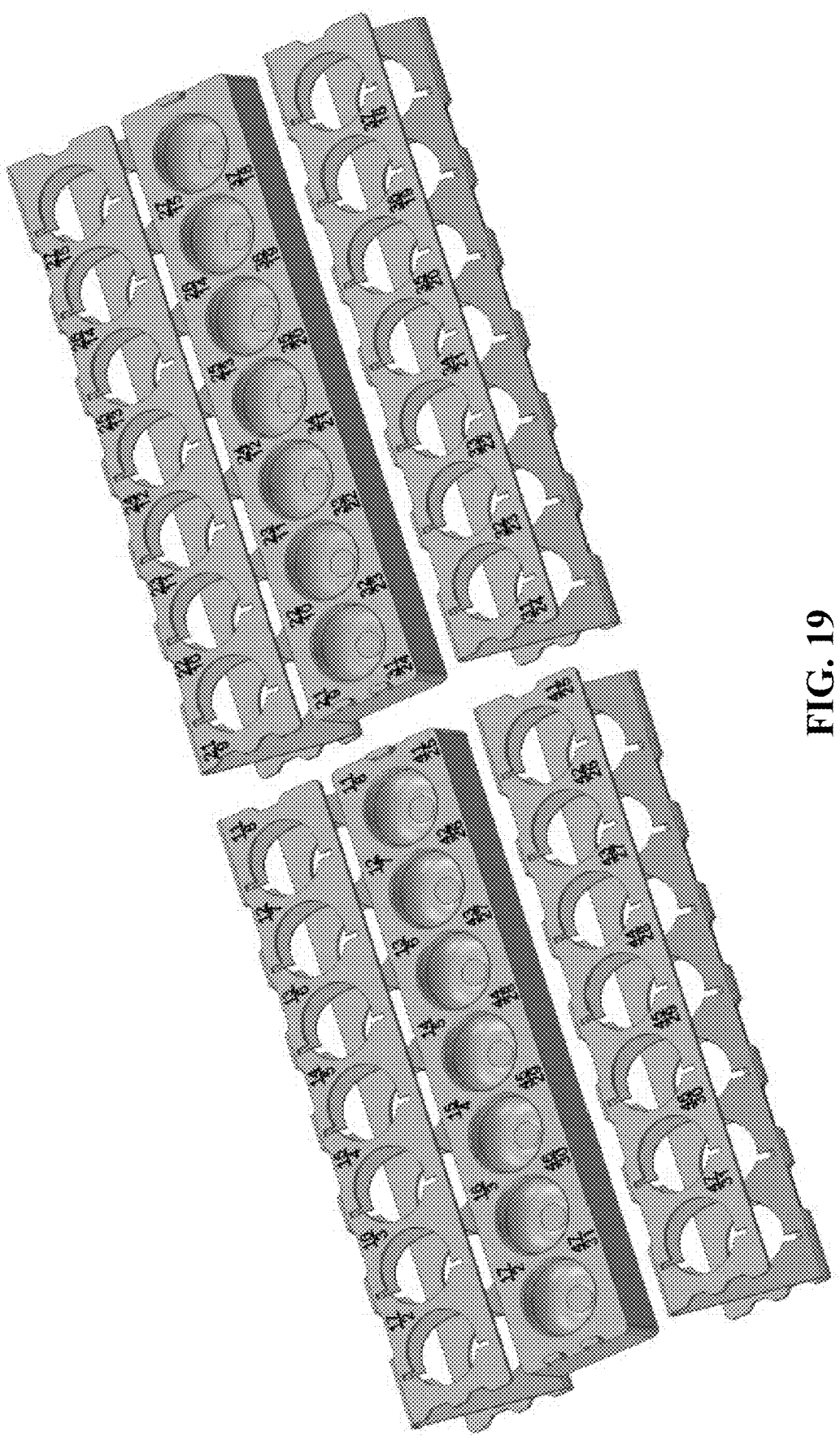
FIG. 19 is yet another exploded view showing two lower rack portions and four upper rack portions, with the four upper portions being numbered for the left and right sides of both the maxillary and the mandible using both the ISO and the Universal tooth numbering systems.

The rack 300 may be formed to organize and support a dental implant container/package for each tooth, as described hereinabove, and thus may include a corresponding number of receptacles (e.g., 32 receptacles including molars, or 28 receptacles since implants are not typically placed at the molar locations, or 14 receptacles per rack where two racks may be used for the upper and lower implant containers, etc.). In one embodiment the rack 300 may be formed to organize and support only 7 dental implant containers/packages, and multiple racks (e.g. four racks—see FIG. 19) may conveniently be used.

The upper portion 310 and the base portion 350 of rack 300 may be formed of any suitable material, including, but not limited to, plastic, metal, wood, composites, etc. The base portion 350 may be formed to have a height H, a width W, and a length L. In an embodiment where seven containers/packages are to be supported, the thickness W of the base portion 350 may be formed to include seven recesses R. Many of the dental implant platform containers are cylindrical in shape, so each of the recesses R may be generally cylindrical having a cylinder diameter D. (Note, a fillet radius may be used at the bottom of each recess, as well as a raised central dimple as shown in FIG. 12). Other shapes may also be used for the recesses, which shape may be slightly over-sized, to nonetheless suitably receive the bottom of the dental implant platform containers/packages having a different cross-sectional shape (e.g., a circular shape, a square shape, a pentagon shape, an octagon shape, etc.).

When the multi-purpose rack 300 is used during implant surgery to support dental implant platform containers/packages, each recess R may receive and provide upward support to the bottom of one such container/package.

When the base portion 350 of the multi-purpose rack 300 is separated from the upper portion 310 and is used to perform restorative procedures for dental implants, the recesses may hold the materials associated with those procedures, which may include: healing abutments, final abutments, screws, crowns, veneers, or any other component related to a particular implant site (i.e., tooth number). Therefore, in one embodiment the diameter D of each recess R may be sized to be slightly larger than the typical size/diameter of the dental implant platform containers/packages.

There currently are three principle manufacturers of dental implants—Implant Direct, TRI Dental Implants Int. AG, and Megagen Implant Co. LTD. The dental implant container without any intermediate packaging for the Implant Direct implants is cylindrical overall, having a hollow cylindrical base container portion plus a cap (see FIG. 14), with a diameter $D_B$ of 18 mm (0.71 inches) for the base container portion, a total height $H_T$ of 50 mm (1.97 inches) for the dental implant container (base plus cap secured thereon), an unopened cap height $H_C$ of 15 mm (0.59 inches), leaving a distance from the bottom of the base container portion to the bottom of the cap of $H_T$ minus $H_C$ being 35 mm (1.38 inches). The container without any intermediate packaging for the Megagen implants is substantially the same, but with a diameter $D_B$ of base container portion of 17 mm (0.67 inches). The container without any packaging for the TRI implants is an elongated box shape with rounded corners, with the rectangular cross-sectional shape having sides of 25 mm (0.98 inches) and a height of 50 mm (1.97 in.).

In one embodiment, the diameter D for the recesses in the base 350 may each be at least 17 mm to accommodate the smallest cylindrical containers, and in another embodiment the diameter D may be at least 18 mm to accommodate both the 17 mm and 18 mm diameter base containers in a clearance fit. The recess diameter may preferable not be excessive (e.g., being less than 25 mm) to prevent the containers from being held too loosely so that they may lean over or bounce around when moved, possibly even bouncing out of the openings. Therefore, in one embodiment the recess diameter may preferably be in the range of 23 mm to 25 mm, and in another embodiment may more preferably be between 21 mm and 23 mm, and in yet another embodiment may most preferably be between 19 mm and 21 mm. However, in yet another embodiment the diameter D may thus be at least 36 mm (e.g., 37 mm to 41 mm) to accommodate receiving the elongated box shaped containers if a rectangular shape is not used (e.g., for a square with sides being 25 mm long to be inscribed within a circle, the circle must have a diameter equal to the diagonal of the square, i.e., the square root of 2 multiplied by 25, which is 1.414 times 25, or 35.35 mm). In yet another embodiment the recesses may be square shaped having sides in the range of 36 to 38 mm in length to accommodate all of the different sized and shaped containers. The size may be increased where the rack may desirably hold the container that is still shrouded in the intermediate plastic-cardboard packing (see FIG. 15). The openings P and the recesses R may be equally spaced apart a suitable distance S for ease in grasping of each one of the containers/packages when desirably removed from the rack.

The upper portion 310 of the rack 300 may be formed to include an upper flange 311 to provide lateral support for each of the dental implant platform containers/packages, and a lower flange 321 to provide for releasable coupling of the upper portion to the base portion 350. To suitably receive and support the dental implant platform containers/packages through the upper flange 311 it may be formed with a corresponding plurality of shaped openings P, each of which may be circular and have a diameter D, and each of which may be sized and shaped to correspond (i.e., be aligned with) the corresponding recesses R in the base portion 350, when the upper portion 310 is releasably secured thereto (See FIG. 12). When the recesses R in the base portion 350 are formed to number seven and be spaced apart a particular distance, the openings in each of the flanges of the upper portion 310 may be similarly formed. As noted previously and shown in FIG. 11, the upper portion 310 as well as the recesses R in the lower portion 350 may alternatively have rectangular-shaped openings PR, or octagonal-shaped openings $P_{OC}$, or any other shaped openings that may be suitably sized as discussed above to receive the dental implant platform containers/packages. It may be preferable to use circular openings in the upper portion 310 with circular recesses; however, the shape of the openings in the upper portion may be different from the shape used for the recesses in the base portion, and just must be sized appropriately for the particular containers to be held therein.

The lower flange 321 may be formed to contact only a portion of the base portion 350 to be releasably secured thereto. Alternatively, the lower flange 321 may be formed similar to the upper flange 311 and may be formed with a generally rectangular shape having the plurality of openings P that are similarly aligned with the corresponding recesses R in the base portion 350, when the upper portion 310 is releasably secured thereto.

The upper flange 311 is may be spaced apart from the lower flange 321 a particular range of distances, and/or may be spaced apart an optimal distance to provide the above-noted lateral support at a suitable uppermost position on the containers/packages.

Where the upper rack portion 310 is to be used by itself, as shown in FIG. 14A, its height $H_{310}$ may be at least the distance from the bottom of the base container portion to the bottom of the cap, i.e., $H_T$ minus $H_C$ being 35 mm or 1.38 inches); therefore if used only by itself the upper rack portion 310 may suitably be formed to have a height $H_{310}$ between the top of the lower flange 321 and the top of the upper flange 311 of 36 mm to 38 mm (1.42 inches to 1.49 inches) in one embodiment, a height $H_{310}$ of 38 mm to 40 mm (1.42 inches to 1.57 inches) in another embodiment, and may have a height $H_{310}$ of 40 mm to 42 mm (1.57 inches to 1.65 inches) in yet another embodiment, and in other embodiments a combination of these ranges or other ranges may alternatively be used. To provide optimal support for the dental implant container by the upper flange 311 of the upper rack portion 310 when used by itself, the height $H_{310}$ may most preferably be between 36 mm to 38 mm, so that the upper flange is as close to the bottom of the cap (i.e., being in close proximity thereto—0.01 mm to 0.03 mm away) as may be achieved through the use of reasonable manufacturing tolerances for the rack and those inherent to the dental implant container.

Where the upper rack portion 310 is used in combination with the base 350 (i.e., the rack 300), as shown in FIG. 14, the height $H_{300}$ from the bottom of each recess R (which are preferably about 0.38" deep) to the top of the upper flange 311 may be at least the distance from the bottom of the base container portion to the bottom of the cap. i.e., $H_T$ minus $H_C$ being 35 mm or 1.38 inches); therefore the height $H_{300}$ may suitably be formed to be 36 mm to 38 mm (1.42 inches to 1.49 inches) in one embodiment, or 38 mm to 40 mm (1.42 inches to 1.57 inches) in another embodiment, or 40 mm to 42 mm (1.57 inches to 1.65 inches) in yet another embodiment, and in other embodiments a combination of these ranges or other ranges may alternatively be used. To provide optimal support for the dental implant container by the upper flange 311 of the upper rack portion 310 when used with the base 350, the height $H_{300}$ may most preferably be between 36 mm to 38 mm, so that the upper flange is as close to the bottom of the cap as may be achieved through the use of reasonable manufacturing tolerances for the two rack portions and those inherent to the dental implant container.

Any suitable structure may be used to space apart the upper flange 311 from the lower flange 321, including, but not limited to: a plurality of posts (note that the use of the posts received within holes in the base may obviate the need for the lower flange), or a single vertical flange integrally formed with the upper and lower flanges to form a C-shaped upper section 310, or a pair of vertical flanges integrally formed with the upper and lower flanges to form a hollow rectangular-shaped upper section, etc. In one embodiment, an angled connecting flange 331 may be used, as shown in FIG. 13, which connecting flange may be integrally formed with the upper flange 311 and the lower flange 321 (e.g., by injection molding), for the upper portion 310 to form an elongated Z-shaped member. The angled connecting flange 331 may also be formed to include a plurality of openings P' that may be aligned with the openings in the upper flange 311, and the periphery of the openings P' may be the projection of the openings P in the upper flange in a direction being perpendicular to the plane of lower flange, to permit sliding of the containers (with and without the intermediate packaging) through both sets of opening. The intermediate flange being so formed with openings may provide additional support for maintaining the dental implant containers in an upright position, particularly where the upper portion 310 may be used by itself. The lower flange 321 may also have a plurality of openings P that may also be aligned with the openings in the upper flange 311. The recesses R in the base portion 350 may also be aligned with the openings P in the upper flange when the upper portion 310 is releasably secured thereto. For additional stability, a plurality of connecting members 341 may extend between and connect to each of the upper flange 321, the angled connecting flange 331, and the lower flange 321.

In order to be able to universally receive and support both the stand-alone cylindrical dental implant containers 103C (FIG. 14) and the elongated box-shaped containers 103B (FIG. 16) that do not have additional external packaging (which may tend to be larger), as well as implant containers 103P that are shrouded in intermediate plastic/cardboard packaging (see FIG. 15 and FIG. 11), the upper flange 321, the angled connecting flange 331, and the lower flange 321 may each have slots Ti and Tii formed thereon. The slots Ti and Tii may respectively extend away from opposite sides of the openings P, and may have a distance $D_T$ between the opposite most ends of the slots (see FIG. 12 and FIG. 13). The slots Ti and Tii may enable receiving and supporting of the flanged portions of a dental implant container with intermediate packaging 103P, as shown in FIG. 11 and FIG. 15. In one embodiment the distance $D_T$ may be between 27-29 mm. In another embodiment, to provide greater clearance, the distance $D_T$ may be between 29 mm and 31 mm. In other embodiments, a combination of such ranges or other ranges may be used instead.

Figure 17:
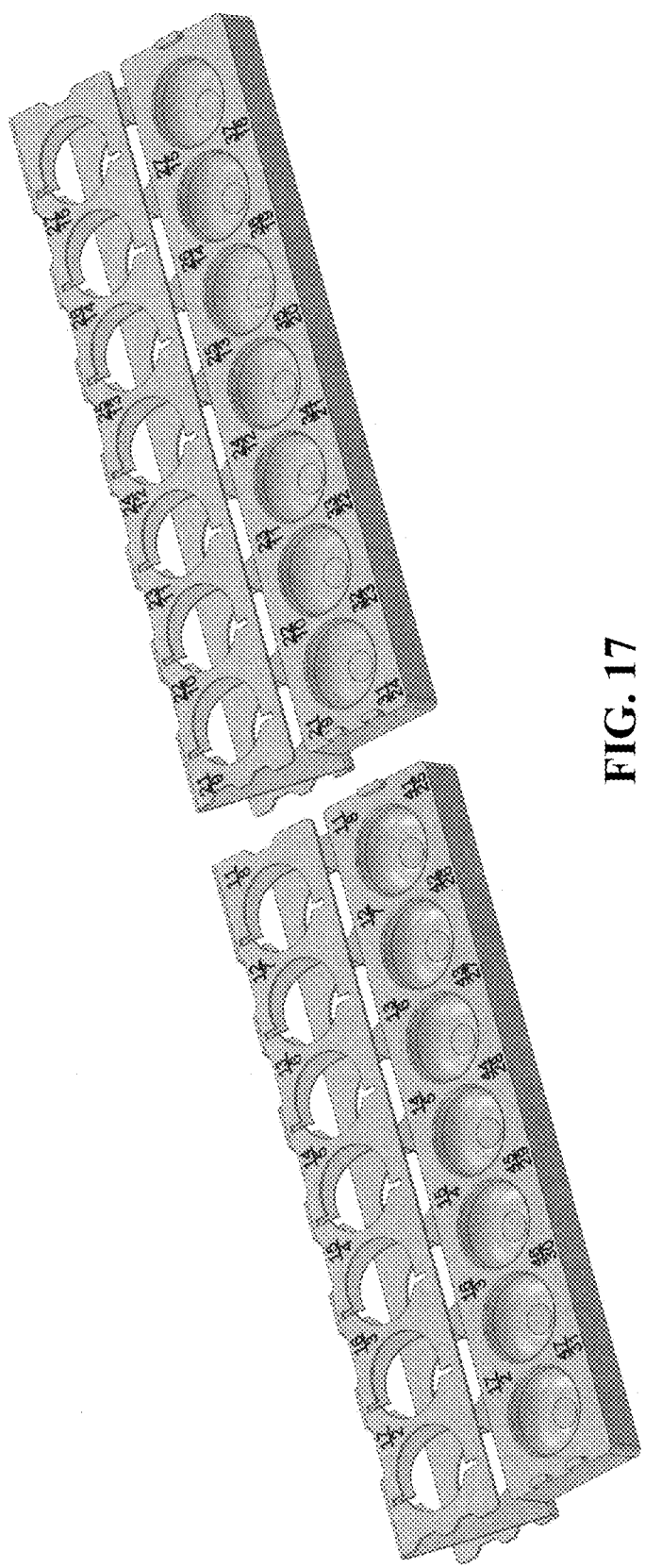
FIG. 17 is an exploded view showing a first rack according to the embodiment of FIG. 9 and a second such rack, with each of the upper and lower portions having been separated, and with the two upper portions being respectively numbered for the left and right sides of the maxillary using both the ISO and the Universal tooth numbering systems.
Figure 18:
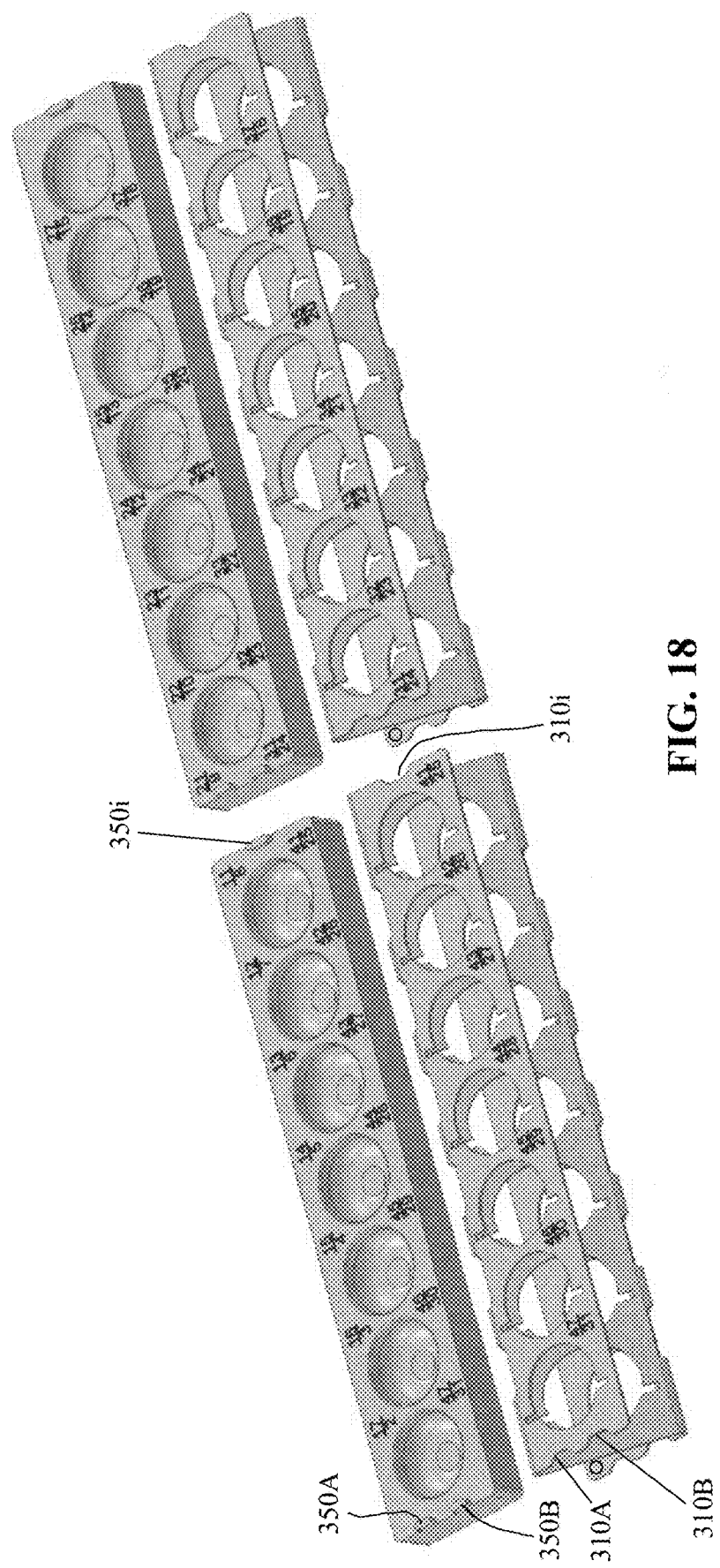
FIG. 18 is another exploded view showing a first rack according to the embodiment of FIG. 9 and a second such rack, with each of the upper and lower portions having been separated, and with the two upper portions being respectively numbered for the left and right sides of the mandible using both the ISO and the Universal tooth numbering systems.

Releasable coupling of the lower flange of the upper portion 310 to the base portion 350 may be accomplished in any suitable manner. In one embodiment, the base portion 350 may be formed with a plurality of protruding cylindrical pegs/pins that may be received in corresponding holes in the lower flange 321 of the upper portion 310 or vice versa (see e.g., U.S. Pat. No. 5,408,189 to Start). In another embodiment, a plurality of small magnets 350M may be secured to the base portion 350 (e.g., proximate to its corners, and being received in holes formed therein) and a plurality of small magnets 310M may be correspondingly secured to the lower flange 321 of the upper portion 310 to accomplish the releasable coupling. In a further embodiment at least a portion of the base portion 350 and at least a portion of the lower flange 321 may be formed of magnetic materials configured to releasably couple the base portion and the upper portion 310 together using magnetism. In yet another embodiment, flanged stops may be formed to protrude from each end of the base portion 350, while corresponding notches may be formed at the edge of each end of the lower flange 321. To permit the lower flange 321 of the upper portion 310 to be keyed to the base portion 350, one end of the base portion may be formed with two flanged stops 350A and 350B, and the other end of the base may be formed with a single flanged stop 350i (FIG. 17), while the lower flange of the upper portion may be formed with two corresponding notches 310A and 310B at one end and one corresponding notch 310i at the other end. A combination of such features may also be used. The upper portion 310 is preferably uniquely keyed to the base portion 350 for each of the left side rack and the right side rack (left-side teeth and right-side teeth). Thus, when the upper portions are removed from the lower portions during a dental implant restoration procedure and are later reattached, the unique key aspect prevents inadvertent securing of the upper portion of the left side on the base that is used and numbered for the right side.

Indicia to indicate the tooth number of the implant containers/packages may be used on either or both of the upper portion 310 and the lower portion 350 as described hereinabove, or as shown in FIG. 11 and FIGS. 17-19. The numbering may be indicative of the left and right sides of the maxillary using both the ISO and the Universal tooth numbering systems. Note that the ISO numbering system (i.e., the International Standards Organization designation system promulgated by the World Health Organization) has a two digit designation, where the first digit represents the quadrant in the mouth (i.e., I=upper right quadrant, 2=upper left quadrant. 3 lower left quadrant, and 4=lower right quadrant), and the second digit counts beginning at the front of the mouth (i.e., tooth number 18 is the molar tooth on the upper right quadrant).

The examples and descriptions provided merely illustrate a preferred embodiment of the present invention. Those skilled in the art and having the benefit of the present disclosure will appreciate that further embodiments may be implemented with various changes within the scope of the present invention. Other modifications, substitutions, omissions and changes may be made in the design, size, materials used or proportions, operating conditions, assembly sequence, or arrangement or positioning of elements and members of the preferred embodiment without departing from the spirit of this invention.

What is claimed is:

1. An organizer rack configured to house and arrange a plurality of dental implant containers, said organizer rack comprising:
   an upper flange with a plurality of shaped openings formed therein, each of said plurality of shaped openings configured to receive the dental implant container therethrough when removed from its intermediate packaging;
   a lower flange configured to support the dental implant containers;
   a connecting flange configured to extend from and be joined to a portion of each of said lower flange and said upper flange to support a top of said upper flange at a distance away from a top of said lower flange to position a bottom of the cap of the dental implant container in close proximity to a top of said upper flange;
   wherein said shaped openings are sized and shaped to support the dental implant container in a substantially upright positions;
   wherein said upper flange and said lower flange are substantially parallel and each have a first side and a second side, and wherein said connecting flange is angled from said first side of said lower flange to said second side of said upper flange to form a z-shaped cross-section;
   wherein said connecting flange comprises a plurality of said openings each being aligned to respectively correspond with said plurality of shaped openings in said upper flange, for said connecting flange to receive the dental implant container therethrough when removed from its intermediate packaging;
   further comprising a base portion removably coupled to and aligned with said lower flange, and configured for a restorative procedure for dental implants;
   wherein said lower flange comprises a plurality of openings each aligned to respectively correspond with said plurality of shaped openings in said upper flange;
   wherein said base portion comprises a plurality of recesses configured to hold one more materials associated with the restorative procedure for dental implants; and
   wherein said plurality of recesses are aligned to respectively correspond with said plurality of shaped openings in said upper flange, with a bottom of each recess in said base portion being configured to receive and provide upward support to a bottom portion of the dental implant container when removed from its intermediate packaging.

2. The organizer rack according to claim 1, wherein each said shaped opening in said upper flange comprises a first slot and a second slot, said first slot configured to extend away from a first side of said shaped opening, and said second slot configured to extend away from a second side of said shaped opening being directly opposite and substantially aligned with said first slot, said shaped opening and said first and second slots configured to receive the dental implant container therethrough when housed within its intermediate packaging.

3. The organizer rack according to claim 2, further comprising a plurality of magnets on said lower flange, and a plurality of magnets on said base portion being correspondingly positioned to removably couple and align said lower flange with said base portion.

4. The organizer rack according to claim 2, wherein at least a portion of said lower flange and at least a portion of said base portion each comprise a magnetic material configured to removably couple said lower flange to said base portion.

5. The organizer rack according to claim 2, further comprising a plurality of holes on said lower flange, and a plurality of pins on said base portion being correspondingly positioned to removably couple and align said lower flange with said base portion.

6. The organizer rack according to claim 2,
wherein said base portion comprises a protruding flange at a first end of said base portion and a pair of protruding flanges at a second end of said base portion;
wherein said lower flange comprises a notch at a first end of said lower flange, and a pair of notches at a second end of said lower flange; and
wherein said protruding flanges and said notches are configured to removably couple and align said lower flange with said base portion.

7. The organizer rack according to claim 2, further comprising means for removably coupling and aligning said lower flange with said base portion.

8. The organizer rack according to claim 2, wherein a distance $D_T$ between opposite ends said first and second slots is between 27-29 mm, to support the intermediate packaging of the dental implant container.

9. The organizer rack according to claim 1, said connecting flange is configured to support said top of said upper flange at a distance away from said top of said lower flange being between 40 mm and 42 mm.

10. The organizer rack according to claim 1, said connecting flange is configured to support said top of said upper flange at a distance away from said top of said lower flange being between 38 mm and 40 mm.

11. The organizer rack according to claim 1, said connecting flange is configured to support said top of said upper flange at a distance away from said top of said lower flange being between 36 mm and 38 mm.

12. The organizer rack according to claim 1, wherein said shaped openings comprise circular-shaped openings with a diameter between 19 mm and 21 mm to receive the dental implant container when removed from its intermediate packaging.

13. The organizer rack according to claim 1, wherein said connecting flange, said upper flange, and said lower flange are integrally formed.

14. The organizer rack according to claim 1, wherein said openings are formed substantially in line.

15. The organizer rack according to claim 1, wherein said plurality of openings in said upper flange comprises at least seven openings.

* * * * *